US011110197B2

(12) United States Patent
Xia et al.

(10) Patent No.: US 11,110,197 B2
(45) Date of Patent: Sep. 7, 2021

(54) SURGICAL SUTURE MATERIALS WITH POROUS SHEATHS FOR DRUG DELIVERY

(71) Applicants: GEORGIA TECH RESEARCH CORPORATION, Atlanta, GA (US); WASHINGTON UNIVERSITY, St. Louis, MO (US)

(72) Inventors: Younan Xia, Atlanta, GA (US); Jianhua Li, Atlanta, GA (US); Stavros Thomopoulos, New York, NY (US); Stephen Linderman, St. Louis, MO (US); Chunlei Zhu, Atlanta, GA (US)

(73) Assignees: Georgia Tech Research Corporation, Atlanta, GA (US); Washington University, St. Louis, MO (US)

( * ) Notice: Subject to any disclaimer, the term of this patent is extended or adjusted under 35 U.S.C. 154(b) by 124 days.

(21) Appl. No.: 16/078,058

(22) PCT Filed: Feb. 24, 2017

(86) PCT No.: PCT/US2017/019365
§ 371 (c)(1),
(2) Date: Aug. 21, 2018

(87) PCT Pub. No.: WO2017/147431
PCT Pub. Date: Aug. 31, 2017

(65) Prior Publication Data
US 2019/0099513 A1    Apr. 4, 2019

Related U.S. Application Data

(60) Provisional application No. 62/299,168, filed on Feb. 24, 2016.

(51) Int. Cl.
*A61L 17/14*    (2006.01)
*A61L 17/04*    (2006.01)
(Continued)

(52) U.S. Cl.
CPC .............. *A61L 17/14* (2013.01); *A61L 17/005* (2013.01); *A61L 17/04* (2013.01); *A61L 17/10* (2013.01); *A61B 17/06166* (2013.01)

(58) Field of Classification Search
CPC ................... A61B 17/06166–2017/0619; A61L 17/00–145
See application file for complete search history.

(56) References Cited

U.S. PATENT DOCUMENTS

| | | | | |
|---|---|---|---|---|
| 2,591,063 | A | * | 4/1952 | Goldberg ......... A61B 17/06166 606/231 |
| 3,669,792 | A | * | 6/1972 | Mitsukawa .......... D06N 3/0086 156/249 |

(Continued)

OTHER PUBLICATIONS

"Young's Modulus." Wikipedia, Wikimedia Foundation, Mar. 11, 2020, en.wikipedia.org/wiki/Young%27s_modulus.*
(Continued)

*Primary Examiner* — Tan-Uyen T Ho
*Assistant Examiner* — Charles M Wei
(74) *Attorney, Agent, or Firm* — Meunier Carlin & Curfman LLC

(57) ABSTRACT

Disclosed herein are surgical suture materials that facilitate the sustained delivery of releasable components. The suture materials are processed by the disclosed methods to create a layer of pores extending inward from the outer surface of the suture. Particularly, the surgical suture materials are swollen in a calcium-ion containing solution, then freeze-dried to create pores which can be filled with a releasable component for ultimate delivery to the tissue. In one particular embodiment, the suture has an outer sheath that defines a lumen. Elongated filaments extend through the lumen. This suture embodiment is processed by the disclosed methods to yield a surgical suture material with a porous outer sheath. The pores enable efficient loading of a releasable component into (Continued)

the lumen, facilitating sustained delivery of the releasable component from the suture. The suture maintains its mechanical integrity despite the introduction of pores due to coordination bonds formed between the calcium ions of the swelling solution and carbonyl oxygen atoms of the polymer chains of the surgical suture material.

18 Claims, 23 Drawing Sheets

(51) Int. Cl.
    *A61L 17/10*         (2006.01)
    *A61L 17/00*         (2006.01)
    *A61B 17/06*         (2006.01)

(56) References Cited

U.S. PATENT DOCUMENTS

| | | | | |
|---|---|---|---|---|
| 4,141,087 | A * | 2/1979 | Shalaby | A61B 17/06133 528/307 |
| 4,280,954 | A * | 7/1981 | Yannas | A23J 1/10 530/356 |
| 4,546,152 | A * | 10/1985 | Koelmel | A61L 17/105 525/437 |
| 4,550,730 | A * | 11/1985 | Shalaby | A61L 15/26 128/897 |
| 4,867,934 | A * | 9/1989 | Repetti | B01D 69/08 264/41 |
| 4,880,002 | A * | 11/1989 | MacGregor | A61B 17/06166 606/226 |
| 5,006,247 | A * | 4/1991 | Dennison | B01D 69/02 210/500.38 |
| 5,836,962 | A * | 11/1998 | Gianotti | A61F 2/90 623/1.51 |
| 5,919,473 | A * | 7/1999 | Elkhoury | A61K 31/454 424/422 |
| 5,980,889 | A * | 11/1999 | Butler | A61K 9/0024 424/423 |
| 6,471,689 | B1 * | 10/2002 | Joseph | A61L 29/16 604/892.1 |
| 8,118,834 | B1 * | 2/2012 | Goraltchouk | A61B 17/06166 606/228 |
| 8,876,864 | B2 * | 11/2014 | Spedden | A61B 17/06166 606/228 |
| 8,901,347 | B1 * | 12/2014 | Bezwada | A61K 47/16 560/359 |
| 8,951,284 | B2 * | 2/2015 | Graziano | A61B 17/06166 606/228 |
| 2004/0161442 | A1 * | 8/2004 | Zamora | A61L 15/28 424/423 |
| 2005/0125034 | A1 * | 6/2005 | Cichocki, Jr. | A61B 17/06166 606/222 |
| 2005/0196746 | A1 * | 9/2005 | Xu | G01N 33/48728 435/4 |
| 2006/0029955 | A1 * | 2/2006 | Guia | B65B 31/00 435/6.11 |
| 2006/0182778 | A1 * | 8/2006 | Balar | A61B 17/06166 424/423 |
| 2006/0275273 | A1 * | 12/2006 | Seyedin | A61L 27/54 424/93.7 |
| 2008/0051881 | A1 * | 2/2008 | Feng | A61L 17/06 623/1.39 |
| 2008/0287990 | A1 * | 11/2008 | Smit | D07B 1/025 606/228 |
| 2009/0318962 | A1 * | 12/2009 | Spedden | A61B 17/06166 606/228 |
| 2010/0010470 | A1 * | 1/2010 | Bates | A61L 29/16 604/509 |
| 2010/0094318 | A1 * | 4/2010 | Li | B32B 37/20 606/152 |
| 2013/0004541 | A1 * | 1/2013 | Thomopoulos | C07K 14/75 424/400 |
| 2013/0066370 | A1 * | 3/2013 | Spedden | A61L 17/08 606/231 |
| 2013/0317545 | A1 * | 11/2013 | Gross | A61B 17/0401 606/230 |

OTHER PUBLICATIONS

"Ultimate Tensile Strength." Wikipedia, Wikimedia Foundation, Mar. 26, 2020, en.wikipedia.org/wiki/Ultimate_tensile_strength.*
"Chapter 6 Mechanical Behavior." web.nchu.edu.tw/~jillc/me/Ch06%20-%20Mechanical%20Behavior.pdf.*
International Preliminary Report on Patentability issued in International Application No. PCT/US2017/019365, dated Sep. 7, 2018.
International Search Report and Written Opinion dated Jun. 27, 2017, from International Application No. PCT/US2017/019365, 11 pages.
Hattori et al., "Molecular Characterization of Nylon 6,6 and Its Dissolved State in Mixture of Calcium Chloride and Methanol", Polymer Journal, vol. 27, No. 6, pp. 631-644.
Sun, "Study on the Mechanism of Nylon 6,6 Dissolving Process Using CaCl2/MeOH as the Solvent", Chinese Journal of Polymer Science, 1994, vol. 12, No. 1, pp. 57-65.

* cited by examiner

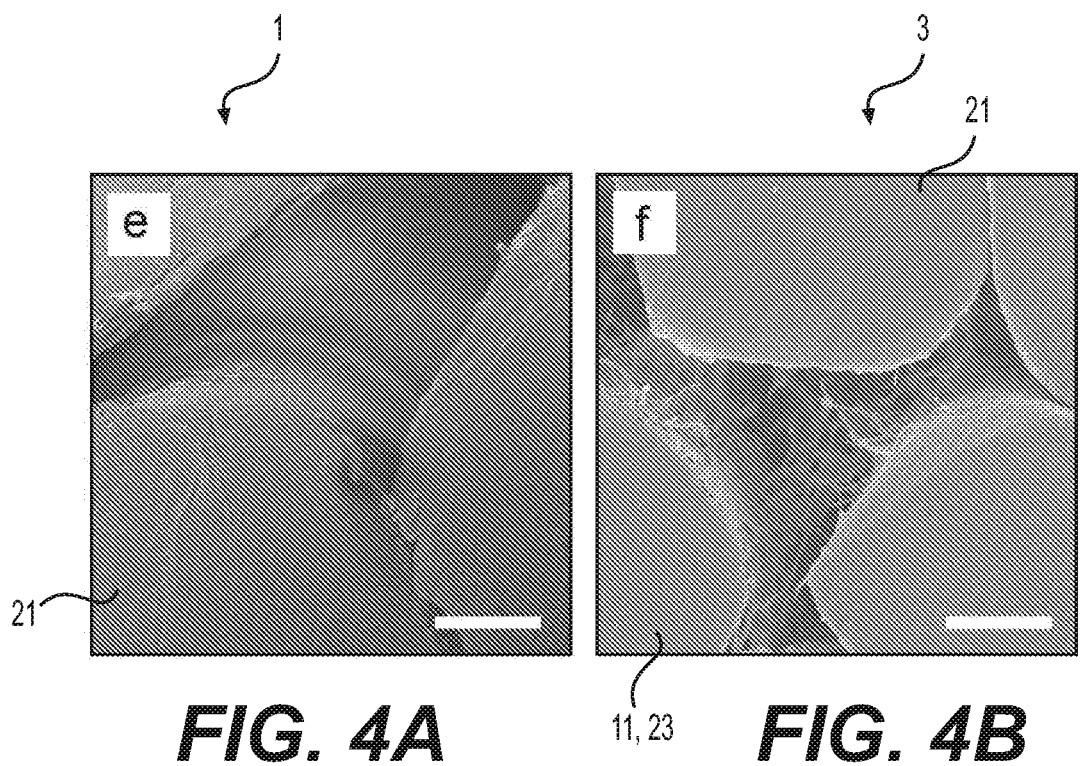
FIG. 4A  FIG. 4B

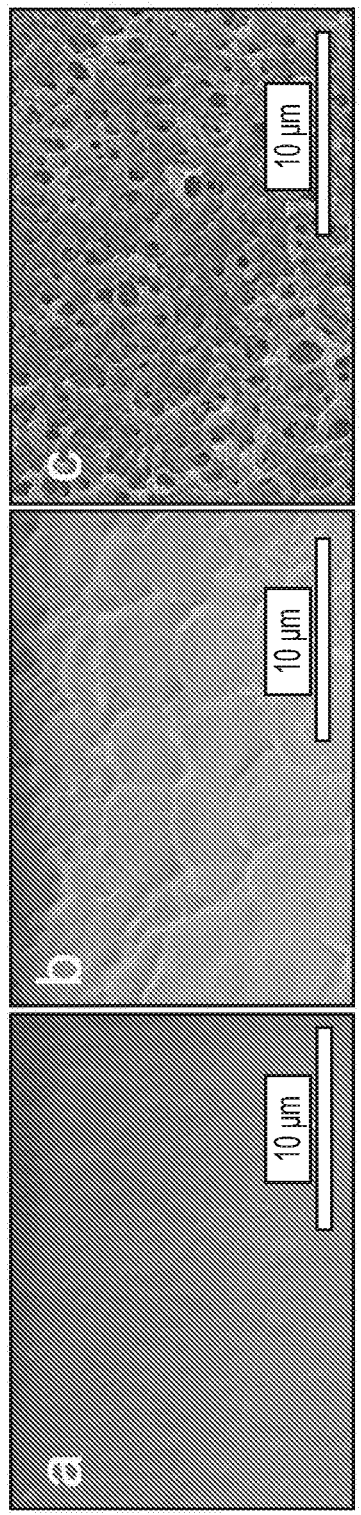
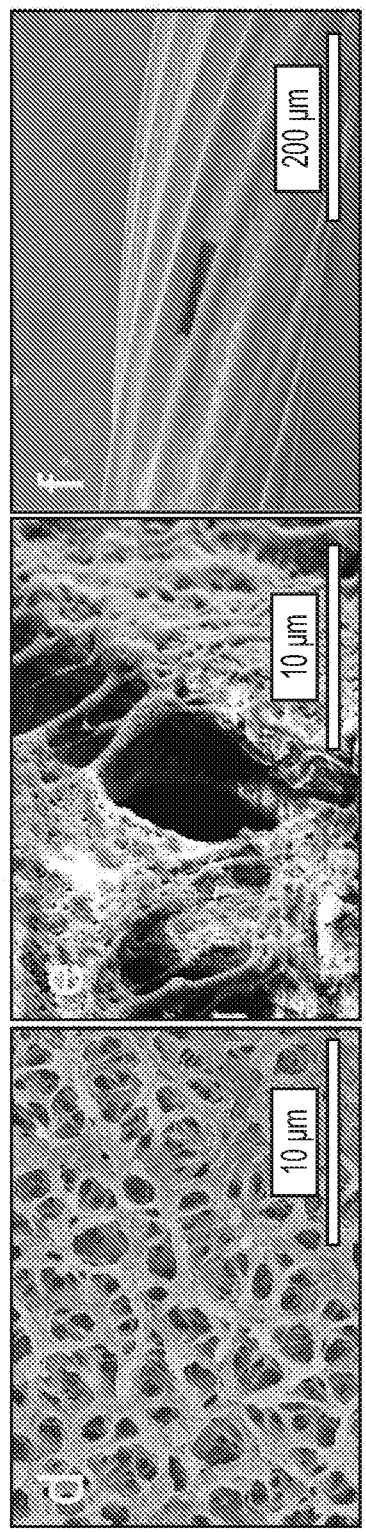

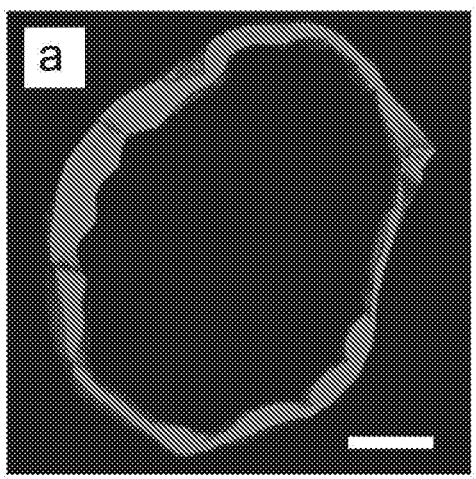
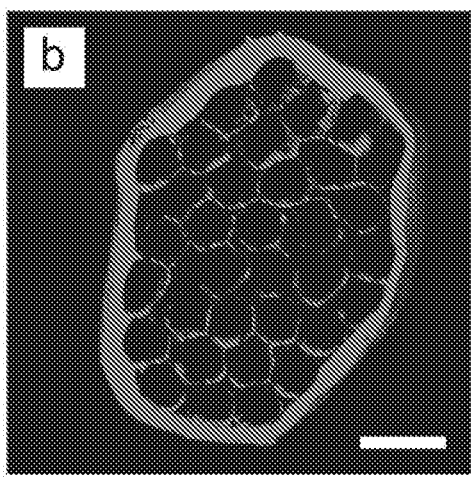
FIG. 8A  FIG. 8B
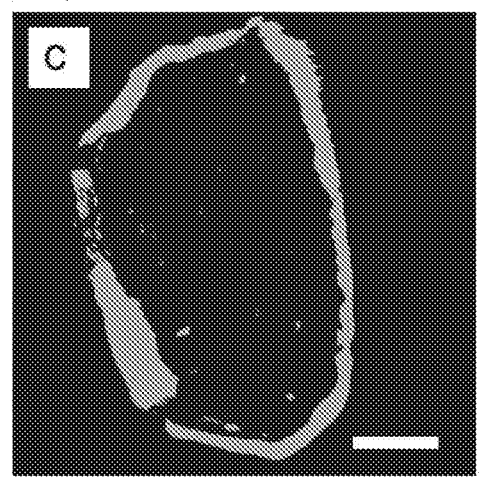
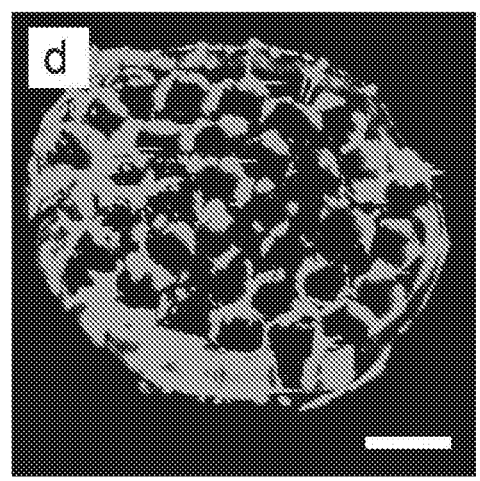
FIG. 8C  FIG. 8D

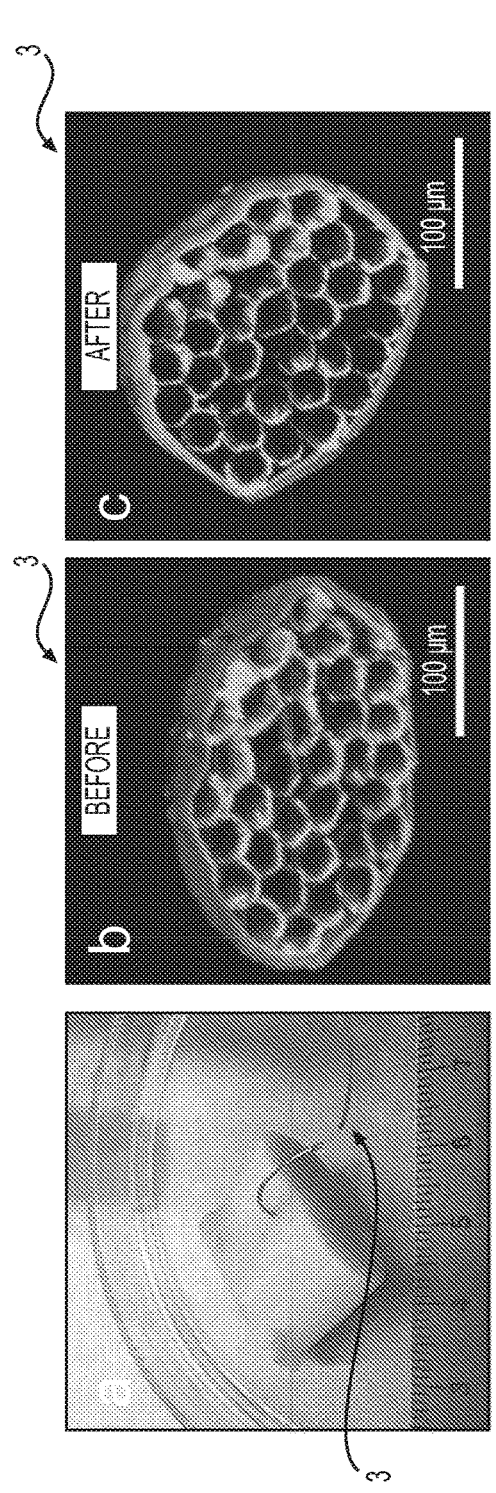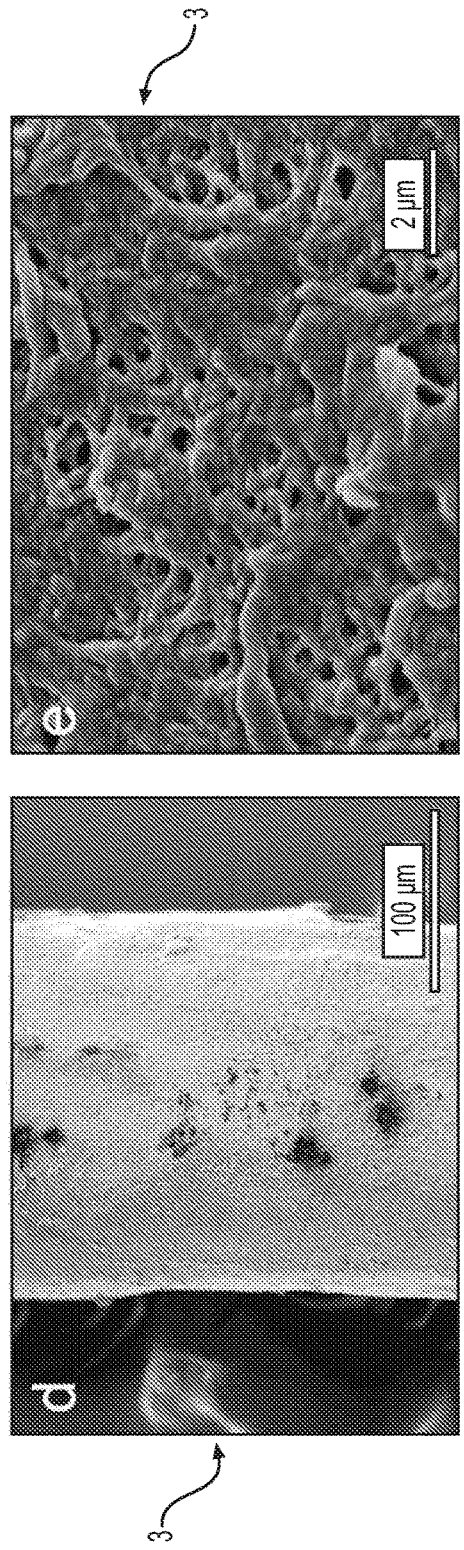

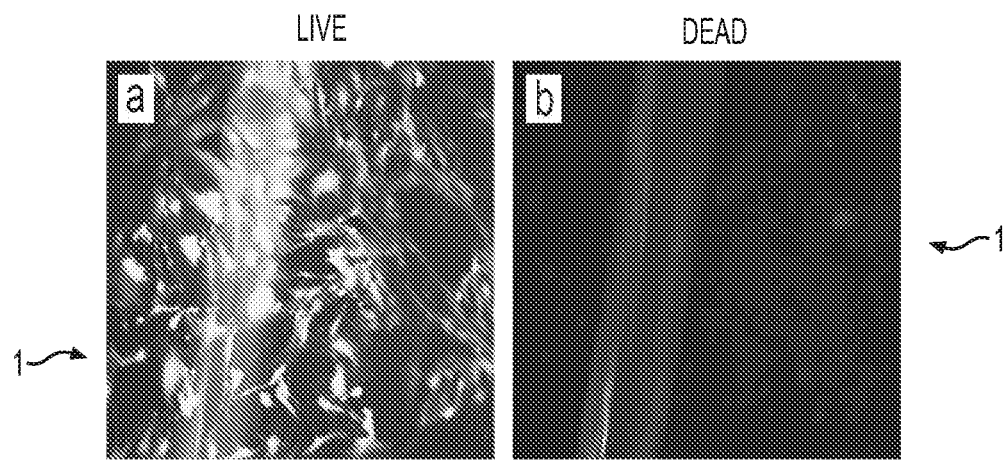
FIG. 14A   FIG. 14B
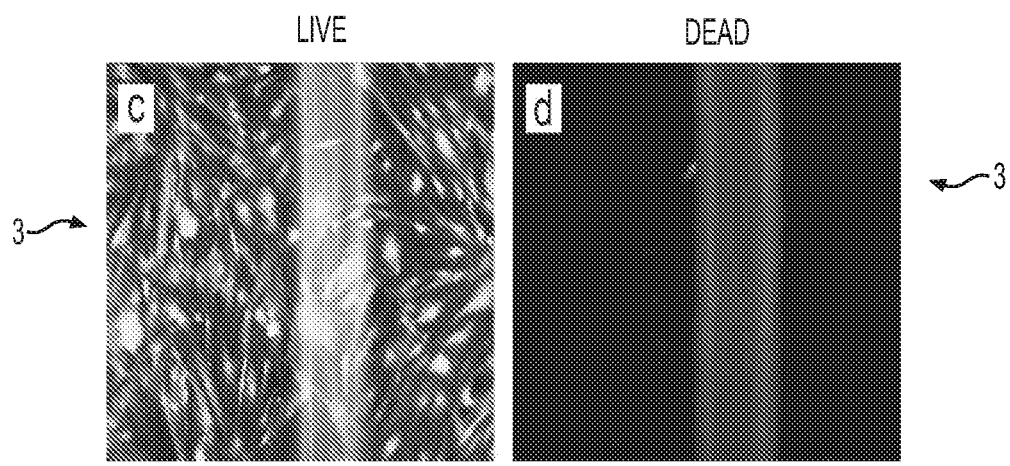
FIG. 14C   FIG. 14D
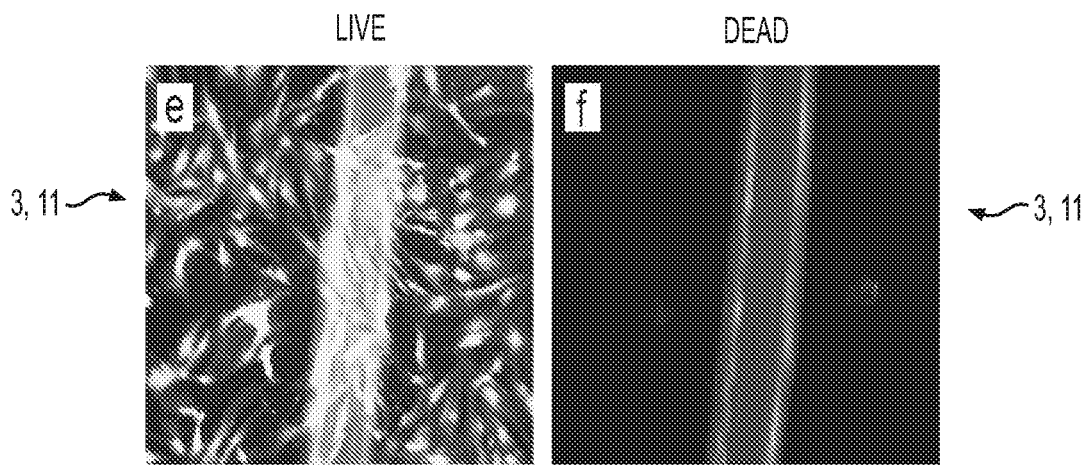
FIG. 14E   FIG. 14F

US 11,110,197 B2

SURGICAL SUTURE MATERIALS WITH POROUS SHEATHS FOR DRUG DELIVERY

RELATED APPLICATIONS

This application is a national stage application filed under 35 U.S.C. § 371 of PCT/US2017/019365, filed Feb. 24, 2017, which claims the benefit of priority to U.S. Provisional Application No. 62/299,168, filed Feb. 24, 2016. Both of these applications are hereby incorporated by reference in their entireties for all purposes.

STATEMENT REGARDING FEDERALLY SPONSORED RESEARCH OR DEVELOPMENT

This invention was made with government support under grant numbers AR060820 and AR062947 awarded by the National Institutes of Health. The government has certain rights in the invention.

FIELD

The present disclosure relates to the field of surgical suture materials, particularly to the loading and sustained delivery of releasable components therefrom.

BACKGROUND

Surgical sutures are widely used to repair tissues. In 2012, the surgical sutures and staples segment accounted for the largest share (55.6%) of total surgical equipment market revenue. Surgical repair of connective tissues such as tendons remains a clinical challenge, primarily due to the failure for the injured site to restore strength within the first three weeks. There are attempts to improve the outcome by increasing the strength of the suture material and modifying the suture grasping method. Although these approaches can improve the initial strength of the repair, they cannot regulate the subsequent biology of healing. In comparison, the tissue engineering strategy, including the use of growth factors, stem cells, and/or scaffolds, provides a great opportunity to improve the efficacy of repair. Specifically, sustained delivery of growth factors to the injured site offers an important strategy for controlling the healing process, which is directed by a complex cascade of biological events modulated by a set of cytokines and growth factors such as platelet derived growth factor (PDGF), vascular endothelial growth factor (VEGF), transforming growth factor β (TGF-β), and basic fibroblast growth factor (bFGF). However, it is a challenge to sustain the delivery of these releasable components over time while maintaining the mechanical integrity of the suture.

SUMMARY

Disclosed herein are surgical suture materials that facilitate the sustained delivery of releasable components. The suture materials are processed by the disclosed methods to create a layer of pores extending inward from the outer surface of the surgical suture material. Particularly, the surgical suture materials are swollen in a calcium-ion containing solution, then freeze-dried to create pores which can be filled with a releasable component for ultimate delivery to the tissue. In one embodiment, the suture has an outer sheath that defines a lumen. Elongated filaments extend through the lumen. This suture embodiment is processed by the disclosed methods to yield a surgical suture material with a porous outer sheath. The pores enable efficient loading of a releasable component into the lumen, facilitating sustained delivery of the releasable component from the suture. The suture maintains its mechanical integrity despite the introduction of pores due to coordination bonds formed between the calcium ions of the swelling solution and carbonyl oxygen atoms of the polymer chains of the surgical suture material.

The surgical suture materials disclosed herein include an elongated outer sheath having an outer surface and an inner surface that defines a lumen. A plurality of elongated filaments are located within the lumen of the elongated outer sheath. The elongated outer sheath also includes a plurality of pores extending between the lumen and the outer surface of the elongated outer sheath. A releasable component is located in the lumen and is able to move from the lumen through one or more pores of the plurality of pores for release from the suture material.

The elongated outer sheath of the surgical suture material comprises a polymer material that includes carbonyl oxygen atoms and calcium ions. In some embodiments, the polymer material is nylon (for example, nylon 6), and carbonyl oxygen atoms of the nylon polymer chains form coordination bonds with the calcium ions. In some embodiments, the elongated outer sheath has a thickness of from about 6 to about 12 micrometers. In some embodiments, the plurality of elongated filaments include a nylon material (for example, nylon-66).

Some embodiments of the surgical suture material can have a modulus that is greater than or equal to 1.4 gigapaschals, an ultimate stress that is greater than or equal to 0.5 gigapaschals, and a strain at maximum stress that is less than or equal to 38%. The pores of the plurality of pores can have diameters ranging from about 200 nanometers to about 100 micrometers, for example, from about 500 nanometers to about 5 micrometers.

Some embodiments of the surgical suture material include a carrier material that is located in the lumen and houses the releasable component. The carrier material can be fibrin, or, for example, fibrin that is configured to provide sustained release of a heparin binding growth factor from the elongated outer sheath. The carrier material housing the releasable component can be located in the pores of the elongated outer sheath. Various types of releasable components may be included. For example, the releasable component can be a small molecule, an ion, a protein, an adhesive, or any combination thereof.

Methods of loading a surgical suture material with a releasable component are also disclosed herein. The methods include the steps of swelling the surgical suture material in a swelling solution comprising calcium ions, freeze-drying the surgical suture material (thereby introducing a plurality of pores that extend inward from an outer surface of the surgical suture material), and filling at least some of the plurality of pores with a releasable component.

In some embodiments, the methods also include exposing the surgical suture material to a carrier material precursor solution comprising the releasable component, filling at least some of the plurality of pores with the carrier material precursor solution, and polymerizing the carrier material precursor solution to form a carrier material. An example carrier material precursor solution can include fibringogen, and polymerizing can include exposing the carrier material precursor solution to thrombin and calcium chloride.

In some method embodiments, the releasable component is connective tissue growth factor (CTGF), and the CTGF concentration in the carrier material precursor solution is less than or equal to 50 micrograms per milliliter. For example, the CTGF concentration can be less than or equal to 30 micrograms per milliliter. In embodiments where the surgical suture material comprises a lumen, the method can include filling at least part of the lumen with the releasable component.

In some method embodiments, the swelling solution includes calcium chloride in methanol. The concentration of calcium chloride in methanol can be 1.6 M or less, or, in some embodiments, 0.5 M or less. Swelling the surgical suture material can include incubating the suture in the swelling solution for from 16 to 28 hours, or, in some embodiments, from 20 to 28 hours.

Freeze-drying the surgical suture material can include freezing the surgical suture material in liquid nitrogen, or in any way that includes freezing the surgical suture material at −97 degrees Celsius or less. Freeze-drying the surgical suture material can also include drying the surgical suture material under a vacuum. In some embodiments, the surgical suture material is sterilized using ethylene oxide gas.

DESCRIPTION OF DRAWINGS

FIGS. 4A-4B show SEM photographs of elongated filaments within the lumen of an unmodified (FIG. 4A) and a modified (FIG. 4B) surgical suture material. The fibrin carrier material is seen in the spaces between the filaments for the modified suture of FIG. 4B. Scale bar=10 micrometers.

FIGS. 6A-6F show SEM photographs of the porous surfaces resulting from various concentrations of calcium chloride in methanol. The unmodified sutures were soaked in methanol containing 0 milliMolar (FIG. 6A), 100 milliMolar (FIG. 6B), 200 milliMolar (FIG. 6C), 500 milliMolar (FIG. 6D), 800 milliMolar (FIG. 6E) and 1000 milliMolar (FIG. 6F) calcium chloride at room temperature for 24 hours, followed by freeze-drying in a vacuum overnight. As shown by the SEM images, both the pore size and porosity increased with increasing calcium ion concentration in the range of 0-500 milliMolar. The porous structure started to collapse in the 800 milliMolar group. The sheath was nearly lost and the inner filaments were visible in the 1000 milliMolar group. The entire suture, including the inner nylon 66 filaments, dissolved in a saturated calcium chloride solution (>2 Molar) in methanol after a few hours at room temperature (not shown).

FIGS. 8A-8D show confocal microscopy photographs of sutures loaded with small molecules (Rhodamine B, FIG. 8A and FIG. 8B) and proteins (FITC-labeled bovine serum albumin (BSA), FIGS. 8C and 8D). The dye is evident in the voids among the inner filaments of the modified suture (FIGS. 8B, 8D). In contrast, dye is nearly absent from the interior of the unmodified suture (FIGS. 8A, 8C). Thus, the modified sutures show greater loading capacity than the unmodified sutures for both small molecules and proteins. Scale bar=50 micrometers.

FIGS. 11A-11E show results of a bovine tendon experiment. FIG. 11A is a photograph of a bovine tendon (thickness: ca. 0.8 centimeters) used in this experiment. Confocal fluorescent imaging of the modified suture loaded with Rhodamine B/fibrin were taken before (FIG. 11B) and after (FIG. 11C) suturing 10 times. No obvious loss of dye was observed after passing the suture through the bovine tendon 10 times. FIG. 11D shows an SEM image of the modified suture loaded with Rhodamine B/fibrin after passing through the bovine tendon 10 times. The sheath remained intact, as shown by the enlarged image in FIG. 11E.

FIG. 13A shows the cumulative release of PDGF from the modified sutures incubated with PDGF at a concentration of 10 micrograms per milliliter (n=3). The unmodified sutures incubated with PDGF at a concentration of 10 micrograms per milliliter served as a reference (n=FIG. 13B shows the correlation between the total amount of PDGF released from the modified sutures for 11 days and the concentration of PDGF used for the loading process (each point is represented by an average value from three individual measurements; $p<0.01$).

FIGS. 14A-14F show confocal microscopy photographs of live (FIGS. 14A, 14C, 14E) and dead (FIGS. 14B, 14D, 14F) human mesenchymal stem cells (hMSCs) on unmodified (FIGS. 14A, 14B), modified (FIGS. 14C, 14D), and modified/PDGF-loaded (FIGS. 14E, 14F) sutures after culture for 72 hours. Note that the suture material also emits red fluorescence under the same excitation light source. No dead cells were seen, indicating that the sutures were non-toxic to hMSCs.

FIG. 18A shows a schematic of the setup. FIG. 18B shows the maximum load and FIG. 18C shows the stiffness. N=11 for the unmodified samples and n=10 for the modified, porous sutures.

DETAILED DESCRIPTION

Figure 1A:
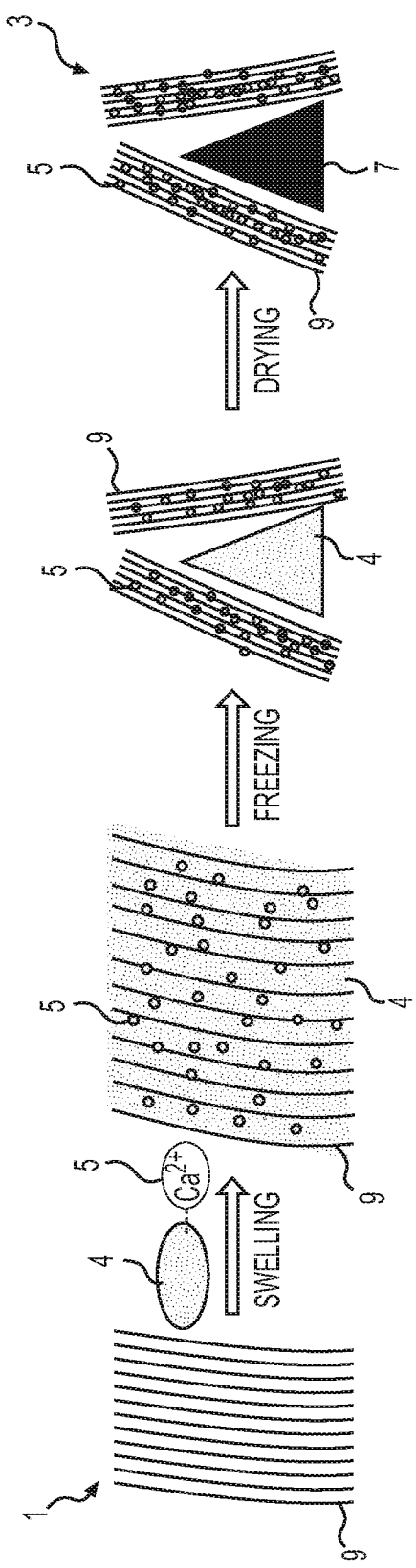
FIG. 1A is a schematic of the swelling and freeze-drying processes. By controlling the swelling time, the outer nylon 6 sheath was made porous without affecting the inner nylon 66 filaments. The methanol in swollen nylon 6 polymer was solidified upon freezing by liquid nitrogen. The polymer chains were expelled from methanol due to phase separation. Finally, after the solvent molecules had sublimated, a suture with a highly porous sheath but intact inner filaments was obtained.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example or and is not intended to convey an indication of" a preferred or ideal aspect. "Such as" is not used in a restrictive sense, but for explanatory purposes.

Sutures are ideal delivery vehicles for releasable components because they are ubiquitously used to provide initial mechanical support for the repair site. Prior work on local delivery of releasable components via sutures has primarily focused on coating the surface of a solid suture thread with a releasable component or releasable component containing material. One major disadvantage of this coating strategy is that almost all of the releasable components are exposed to the surrounding tissue, resulting in the quick release of a large proportion within the first few hours after implantation. Sustained delivery of releasable components from sutures can be achieved using various types of carriers, but most of the reported release profiles remain relatively short. For example, using a carrier based on fatty acid, antiseptic release from braided sutures was only achieved over a period of 100 hours. A second disadvantage of directly coating the surface of a suture is that the amount of releasable component that can be loaded is rather limited. Typically, the releasable component is restricted to a thin coating layer, and the coating can easily peel off during handling due to weak binding between the coating layer and the suture surface. Despite these prior efforts and some marginal success in enhancing tendon healing with releasable component-loaded sutures, there is still a great potential for increasing the dose and time course of suture-based delivery.

Disclosed herein are surgical suture materials that facilitate the sustained delivery of releasable components. The suture materials are processed by the disclosed methods to create a layer of pores extending inward from the outer surface of the suture. Particularly, the surgical suture materials are swollen in a calcium-ion containing solution, then freeze-dried to create pores which can be filled with a releasable component for ultimate delivery to the tissue. In one particular embodiment, the suture has an outer sheath that defines a lumen. Elongated filaments extend through the lumen. This suture embodiment is processed by the disclosed methods to yield a surgical suture material with a porous outer sheath. The pores enable efficient loading of a releasable component into the lumen, facilitating sustained delivery of the releasable component from the suture. The suture maintains its mechanical integrity despite the introduction of pores due to coordination bonds formed between the calcium ions of the swelling solution and carbonyl oxygen atoms of the polymer chains of the surgical suture material.

Figure 1B:
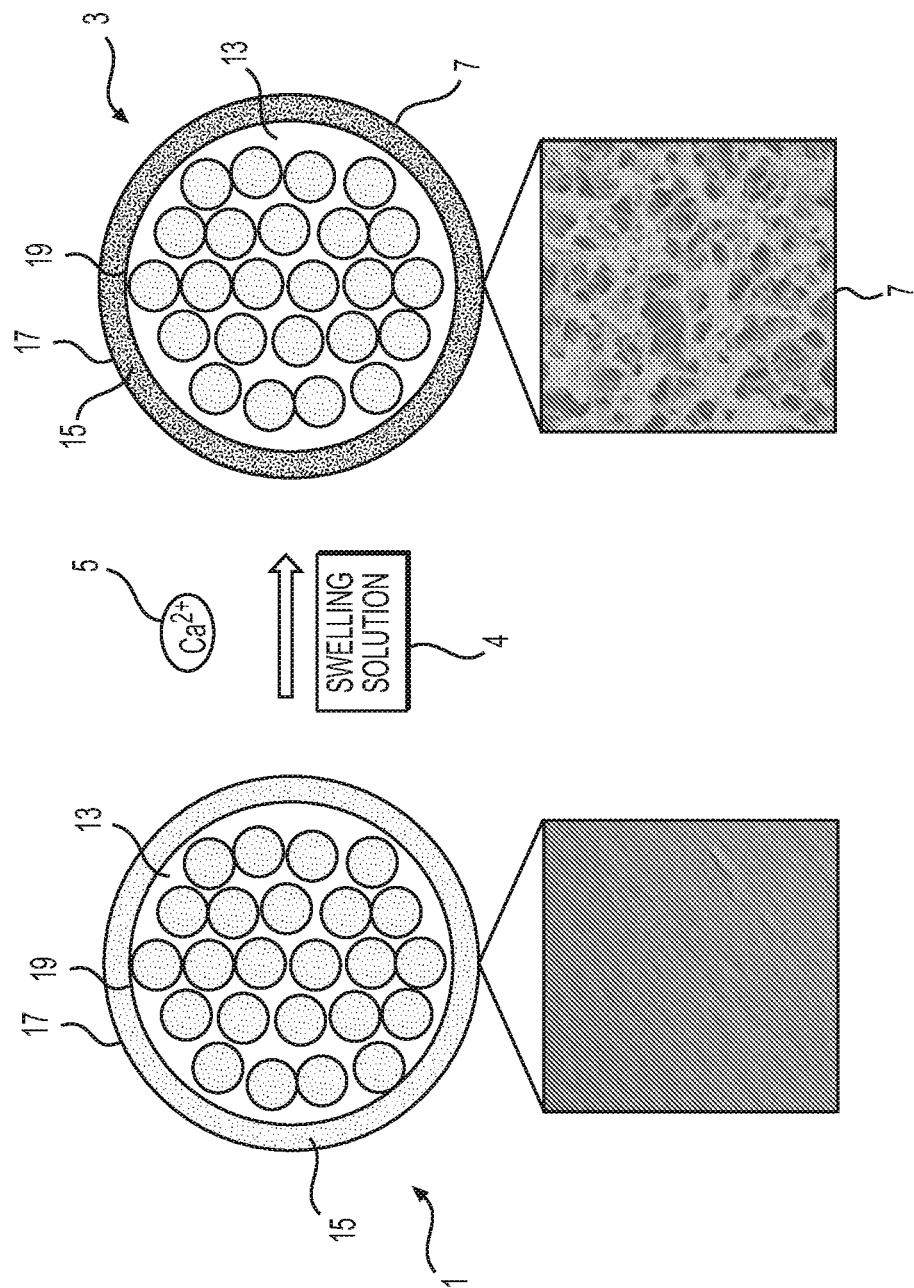
FIG. 1B is a schematic including scanning electron microscopy (SEM) photographs of the structure of the elongated outer sheath before and after the methods of fabricating the porous outer layer.
Figure 1C:
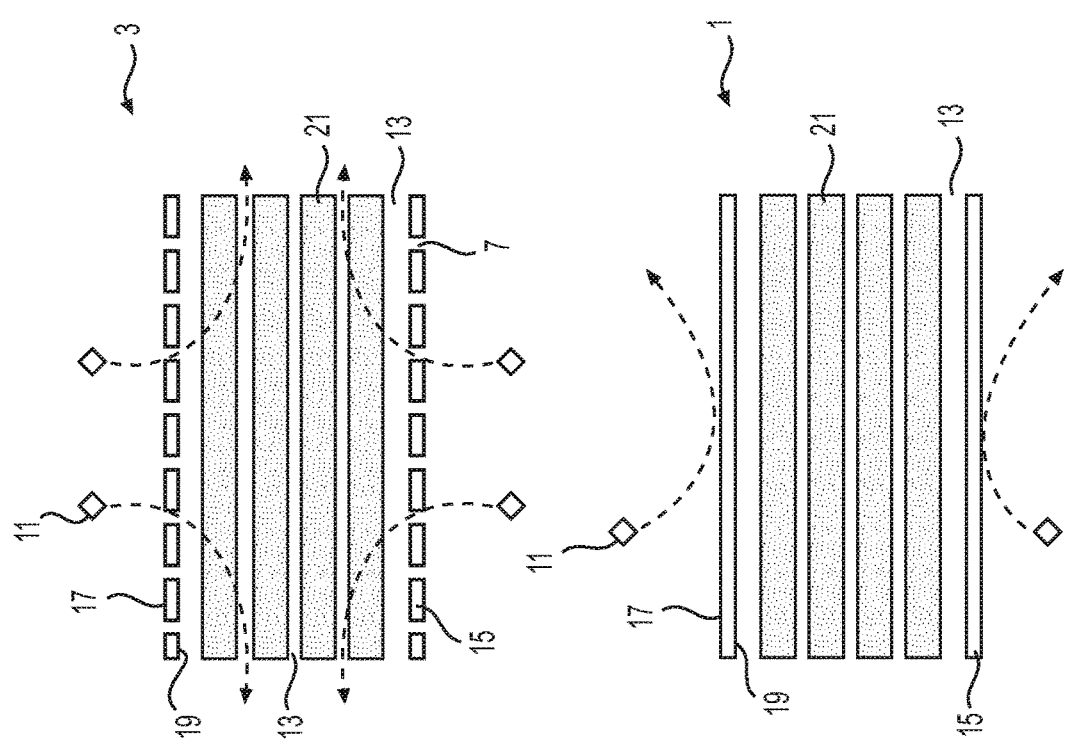
FIG. 1C is a schematic demonstrating the loading of releasable components into an unmodified suture (bottom) and a suture modified by the methods disclosed herein (top).

FIGS. 1A-C show schematics for an example method of loading a surgical suture material with a releasable component. As depicted at the microscopic level in FIG. 1A, a pristine, unmodified surgical suture material 1 is swollen in a swelling solution 4 that contains calcium ions 5, then freeze-dried to create a plurality of pores 7 that extend inward from the outer surface of now modified surgical suture material 3. During swelling, the calcium ions disperse through the polymer chains 9 of the surgical suture material. Freezing causes a phase separation between the polymer chains 9 and the swelling solution 4, but the calcium ions 5 remain dispersed through the polymer chains 9, having formed coordination bonds with carbonyl oxygen atoms therein. During the drying step, the swelling solution 4 sublimates, leaving behind a plurality of pores 7 in the surgical suture material 3. FIG. 1B shows SEM photographs of the surgical suture material before and after the addition of the plurality of pores 7. After the plurality of pores 7 are introduced by the freeze-drying step, the modified surgical suture material 3 is exposed to a releasable component 11, as depicted in FIG. 1C. The releasable component 11 fills the plurality of pores 7 of the modified suture 3 and moves into the inner regions of the suture. In contrast, the releasable component 11 cannot penetrate the outer surface of the unmodified suture 1.

The duration of time that the surgical suture material is exposed to the swelling solution 4 can vary from about 16 to 28 hours. In some embodiments, the duration of time is from 20 to 28 hours. In one embodiment, the surgical suture material includes nylon. Thus, any substance that dissolves or partially dissolves nylon can be used as the swelling solution 4. For example, the swelling solution 4 can be methanol containing calcium chloride. The concentration of calcium chloride can be 1.6 Molar or less, or, in some embodiments, 0.5 Molar or less. The calcium chloride concentration and the duration of the swelling step affect the morphology of the porous structure, as shown in FIGS. 6A-E. The two variables can be tuned to adjust the morphology of the porous structure for a given application. More concentrated calcium chloride solutions can also lead to a more efficient swelling process.

Other swelling solutions can also be used, for example, acids (including, but not limited to, acetic acid, trifluoroacetic acid, formic acid, lactic acid, hydrochloric acid, hydrobromic acid, hydrofluoric acid, hydrofluorosilicic acid, phosphoric acid, nitric acid, sulfuric acid, and/or mineral acids), halogens (including, but not limited to, chlorine, bromine, and/or iodine), phenol or phenol derivatives (including, but not limited to, cresol, xylenol and/or chlorophenol), metallic salts (including, but not limited to calcium hypochlorite). Other potential swelling solutions include, but are not limited to, dimethylformamide, dichloroethylene, dichloromethane, formaldehyde, fluoronated alcohols, hydrogen peroxide, hydrogen sulfide, γ-butyrolactone, nitrobenzene, aniline, resorcinol, trichloroethylene, or any combination or dilution of any of the above listed possible swelling solutions.

The freezing step of the freeze-drying process takes place at a temperature which induces crystallization and thus phase separation of the swelling solution 4 out of the polymer chains 9. For example, if methanol is utilized as the swelling solution, then the freezing temperature can be −97 degrees Celsius or less, which is the melting point of methanol. Likewise, if another swelling solution is used, the freezing temperature should be at the melting point of that swelling solution, or less. In some embodiments, the freezing step of the freeze-drying process can be conducted in liquid nitrogen. The drying step of the freeze-drying process causes sublimation or evaporation of the phase separated swelling solution out of the polymer chains, leaving behind the plurality of pores 7. In some embodiments, the drying step takes place under a vacuum. After freeze-drying, the modified suture 3 can be sterilized by a process that does not alter the pore structure. For example, the modified suture can be sterilized using ethylene oxide gas.

Once introduced by the freeze-drying process, the plurality of pores 7 is at least partially filled with a releasable component 11. If the surgical suture material has a lumen 13 (as depicted in FIGS. 1B and 1C), then the releasable component 11 moves through the plurality of pores 7, at least partially filling the lumen 13 of the surgical suture material. The releasable component 11 can be a protein or peptide (including, but not limited to, a growth factor such as connective tissue growth factor, platelet-derived growth factor, growth factors from the transforming growth factor β family, basic fibroblast growth factor, bone morphogenetic proteins, insulin-like growth factor, vascular endothelial growth factor, growth factors stimulating neuronal differentiation or proliferation, integrins or other collagen-binding proteins or peptides, proteins or peptides that facilitate tissue adhesion, and/or anti-inflammatory antibodies). The releasable component can be a biofactor, which is any factor that elicits a biological response. In some embodiments, the releasable component 11 can be an ion. In some embodiments, the releasable component 11 can be a small molecule (including, but not limited to, antibiotics, antifungals, other antimicrobials, NSAIDs, and/or other anti-inflammatory drugs). In some embodiments, the releasable component 11 can be an adhesive (such as, but not limited to, albumin/glutaraldehyde based adhesives, fibrin based adhesives, cyanoacrylates or cyanoacrylate derivative adhesives, and/or dopamine or other catechol-derived adhesives). In addition to the other listed benefits, the plurality of pores 7 provides protection to the releasable component when the suture is threaded through the tissue, preventing it from being stripped off by friction.

In some embodiments, the releasable component 11 can be dispersed within a carrier material precursor solution to facilitate loading of the releasable component 11 and to adjust the amount of the releasable component that is delivered from the surgical suture material (the dosage). The surgical suture material is exposed to the carrier material precursor solution, such that the precursor solution containing the releasable component 11 fills at least some of the plurality of pores 7. The carrier material precursor solution is then polymerized around the releasable component 11, within the plurality of pores 7, to create a carrier material 23 that dilutes and slows the release of the releasable component 11 from the surgical suture material.

The carrier material 23 can be any material, synthetic or natural, that facilitates the loading and sustains the delivery of the releasable component 11. In some embodiments, the carrier material is a polymer. The carrier material can be a synthetic or a naturally occurring compound, or combinations of two or more synthetic or naturally occurring compounds. Examples of naturally occurring compounds include, but are not limited to, fibrin, collagen, gelatin, chitosan, starch, cellulose, alginate, silk fibroin, heparin, heparin-binding peptides, and/or Matrigel.

In some embodiments, the carrier material precursor solution comprises fibrinogen. The fibrinogen is polymerized to a fibrin carrier material by exposure of the carrier material precursor solution to thrombin and calcium chloride. The fibrin can be modified, in some embodiments, to provide sustained release of a heparin binding growth factor as the releasable component 11. For example, in some embodiments, the releasable component 11 can be CTGF. The concentration of CTGF in the carrier material precursor solution can be, for example, 50 micrograms per milliliter or less.

Figure 2A:
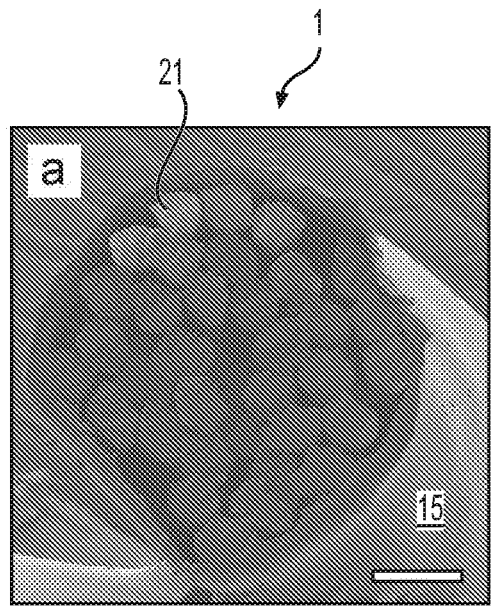
FIGS. 2A-2D show SEM images of the cross sections (FIG. 2A, FIG. 2B) and side surfaces (FIG. 2C, FIG. 2D) of the unmodified (FIG. 2A, 2C) and modified (FIG. 2B, 2D) sutures. Scale bars: 50 micrometers in FIGS. 2A and 2B, 2 micrometers in FIGS. 2C and 2D.
Figure 2B:
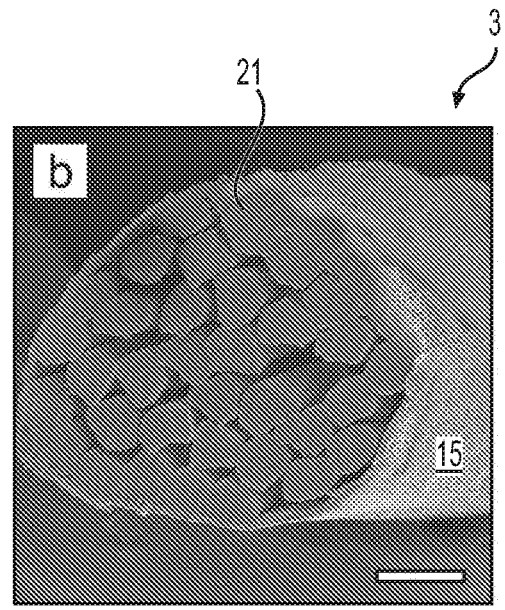
Figure 2C:
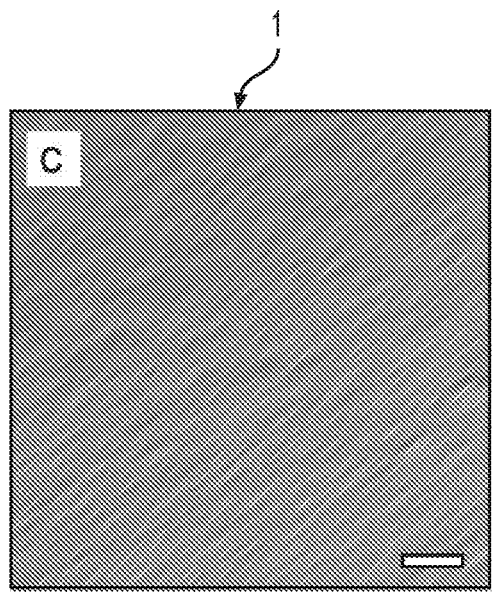
Figure 2D:
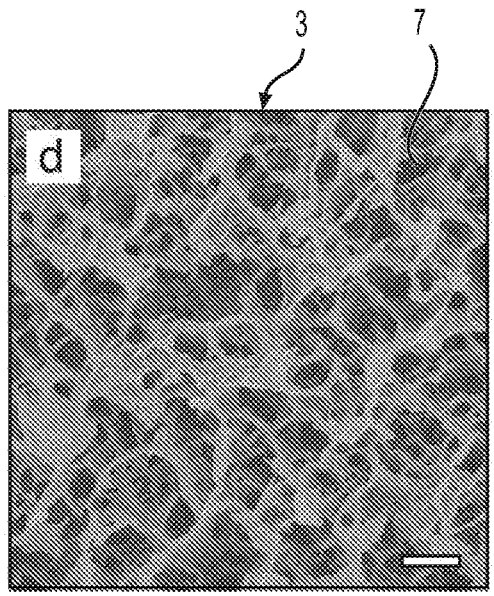

In the exemplary embodiment shown in FIGS. 1B-1C and 2A-2D, the surgical suture material includes an elongated outer sheath 15. The sheath can, in some embodiments, range in thickness from about 6 micrometers to about 12 micrometers. The elongated outer sheath 15 includes an outer surface 17 and an inner surface 19, the inner surface 19 defining lumen 13 as depicted in the schematics of FIGS. 1B and 1C. A plurality of elongated filaments 21 are located within the lumen 13 of the elongated outer sheath 15. After the processing methods described above, the elongated sheath 15 of the modified suture 3 contains a plurality of pores 7 extending between the outer surface 17 and the lumen 13. The pores can range from about 200 nanometers to 100 micrometers. In some embodiments, the range from about 500 nanometers to about 5 micrometers. The unmodified suture 1 is shown at lower and higher magnifications, respectively, in the SEM photographs of FIGS. 2A and 2C. FIGS. 2B and 2D show the modified surgical suture material 3 at lower and higher magnifications, respectively. The plurality of pores 7 is not present prior to the processing steps, as shown in FIG. 2C, but the pores are clearly visible after processing as shown in FIG. 2D.

Importantly, the introduction of the plurality of pores 7 does not reduce the mechanical integrity of the suture, as explained in greater detail in the examples below. For a 4-0 caliber suture or greater, the tensile elastic (Young's) modulus can be, in some embodiments, greater than or equal to 1.4 GPa. The ultimate stress (or strength) can be greater than or equal to 0.5 GPa. The strain at maximum stress can be less than or equal to 38%.

Figure 3A:
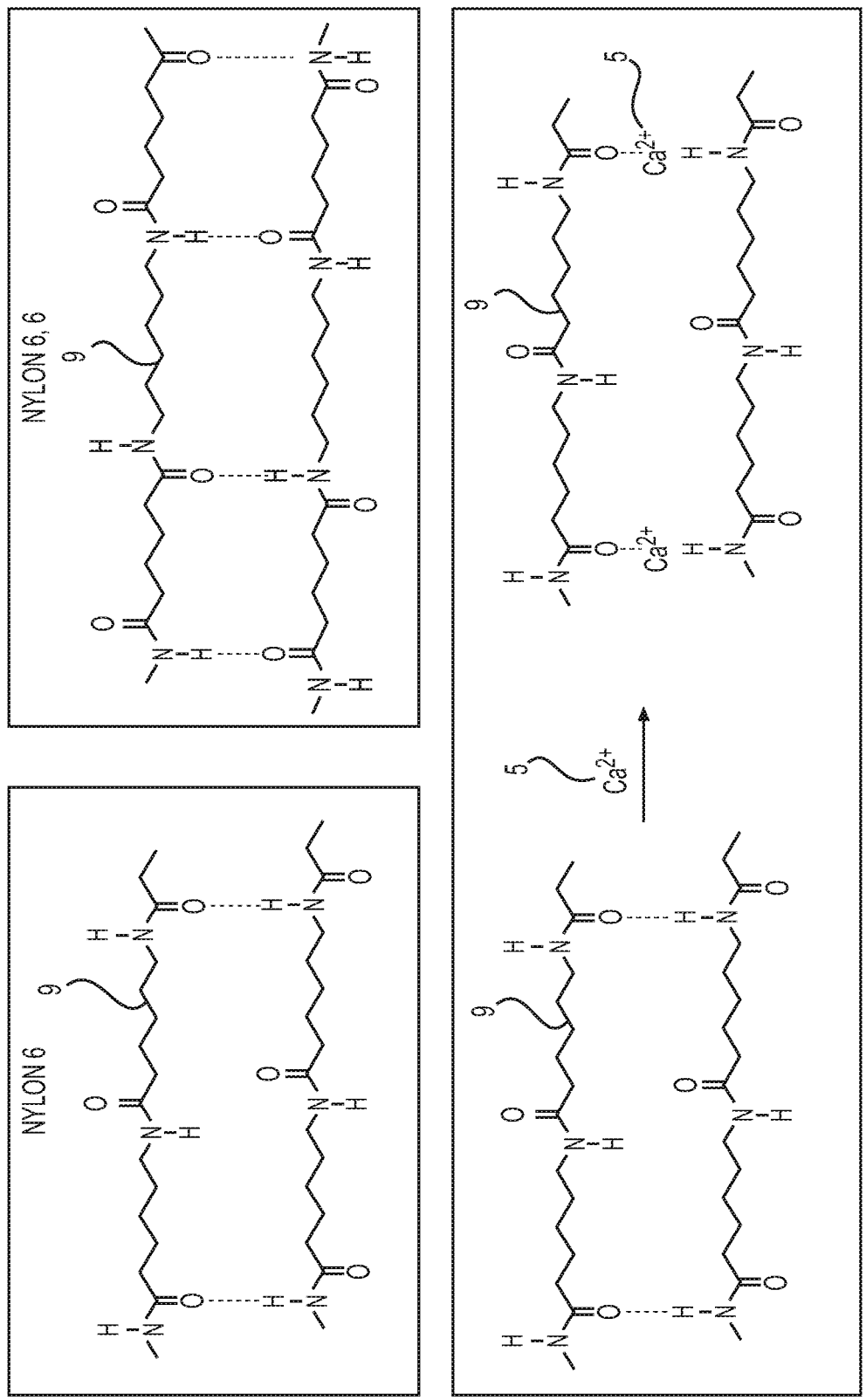
FIG. 3A shows the molecular structures of nylon 6 and nylon 66. The hydrogen bonding between the carbonyl oxygen and amide hydrogen allows the chains to line up and form fibers. Compared with nylon 66, nylon 6 has a more open structure. The calcium ions can break the hydrogen bonds between nylon 6 chains by forming calcium-nylon 6 coordination complexes while the co-introduced methanol is trapped among the polymer chains.

The consistency in mechanical integrity between modified and unmodified sutures is due, at least in part, to coordination bonds that form between the calcium ions 5 introduced by the swelling solution and the carbonyl oxygen atoms of the polymer chains 9 that make up the surgical suture material. An exemplary polymer comprising carbonyl oxygen atoms is nylon. In one embodiment, the elongated outer sheath 15 is formed of nylon 6, and the plurality of elongated filaments 21 are formed of nylon 66. FIG. 3 shows the chemical structures of nylon 6 and nylon 66 before and after the introduction of coordination bonds with calcium ions 5. Another contributing factor to the consistent mechanical properties before and after the modification is that the elongated filaments 21 extending through the lumen of elongated outer sheath 15 are largely unaffected (that is, very few, if any, pores are introduced to the elongated filaments 21). The elongated filaments 21 of the modified surgical suture material 3 have no porosity, negligible porosity, or at least a significantly lower porosity than that of the elongated outer sheath 15.

The releasable component 11 is introduced to the suture during the filling step, as described above. During the filling step, the releasable component 11 (with or without the carrier material precursor solution) fills plurality of pores 7 and the lumen 13 of the modified surgical suture material, as shown in FIG. 1C. FIG. 4B shows the elongated filaments 21 that extend through the lumen 13 of the elongated outer sheath 15. The spaces between the elongated filaments which extend through the lumen are at least partially filled with carrier material 23 and releasable component 11. For contrast, FIG. 4A shows elongated filaments 21 without carrier material 23 and releasable component 11. From the lumen 13, the releasable component 11 can move through the plurality of pores 7 for release from the modified surgical suture material 3.

Example 1

In this example, commercially available sutures (Supramid® 4-0, cable-type, S. Jackson Inc., Alexandria, Va.) were modified for improved delivery of growth factors by achieving efficient loading and sustained release of growth factors without compromising the mechanical integrity of the suture. Specifically, cable-type sutures were partially swollen and then freeze-dried to generate micrometer-sized pores in the sheaths. The sutures chosen for testing were from a class of commercially available polyfilament sutures commonly used for tendon repair. The suture is characterized by a cable-type structure comprising fine inner nylon-6,6 filaments enclosed by a nylon-6 elongated outer sheath with a smooth surface. After modification, the outer sheath became highly porous while the inner filaments remained intact. As such, the voids among the inner filaments were fully accessible and were employed for the loading of releasable components, while the porous sheath served as a physical barrier to slow down the subsequent release process.

Figure 3B:
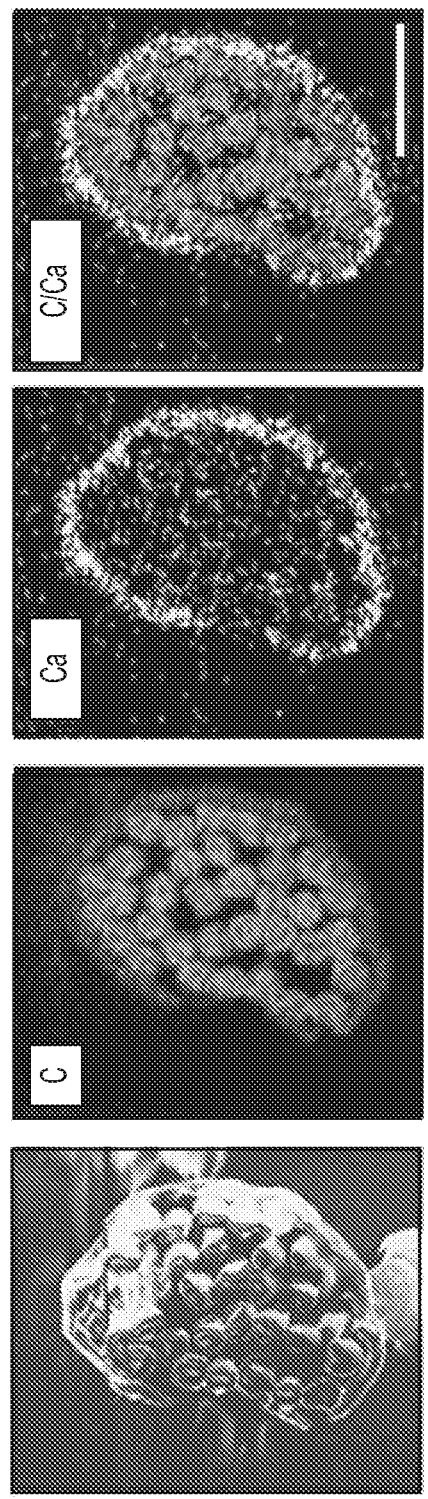
FIG. 3B shows distributions of calcium across the cross-section of a modified suture as revealed by energy-dispersive X-ray spectroscopy (EDX) mapping. Most of the calcium was confined to the porous sheath. Scale bar=100 micrometers. "C" indicates carbon, while "Ca" indicates calcium.

FIG. 1A shows a schematic illustration of the modification procedure, which involves swelling and then freeze-drying the suture. In the first step, the sutures were swollen in a methanol ($CH_3OH$) solution containing calcium chloride ($CaCl_2$). The calcium cations (Ce) formed coordination bonds with the carbonyl groups on nylon, breaking the hydrogen bonds between adjacent nylon chains, as described in "Molecular Characterization of Nylon 6,6 and its Dissolved State in Mixture of Calcium Chloride and Methanol" [1] and "Study on the Mechanism of Nylon 6,6 Dissolving Process Using $CaCl_2$/MeOH as the Solvent" [2], the contents of which are incorporated by reference in their entireties. By controlling the incubation time, most of the swelling was restricted to the sheaths only, before the calcium ions started to attack the inner filaments. To confirm this, the distribution of calcium in a modified suture was characterized by EDX mapping. As shown in FIG. 3B, most of the calcium was confined to the outer sheath. In the next step, the swollen sutures were quickly frozen by transferring them into liquid nitrogen (−196 degrees Celsius). The solvent molecules trapped in the sheaths were crystallized and phase-separated from the polymer chains, eventually producing a highly porous structure once the solvent molecules had been removed by sublimation. The final products were sutures with highly porous sheaths and intact inner filaments.

Figure 5:
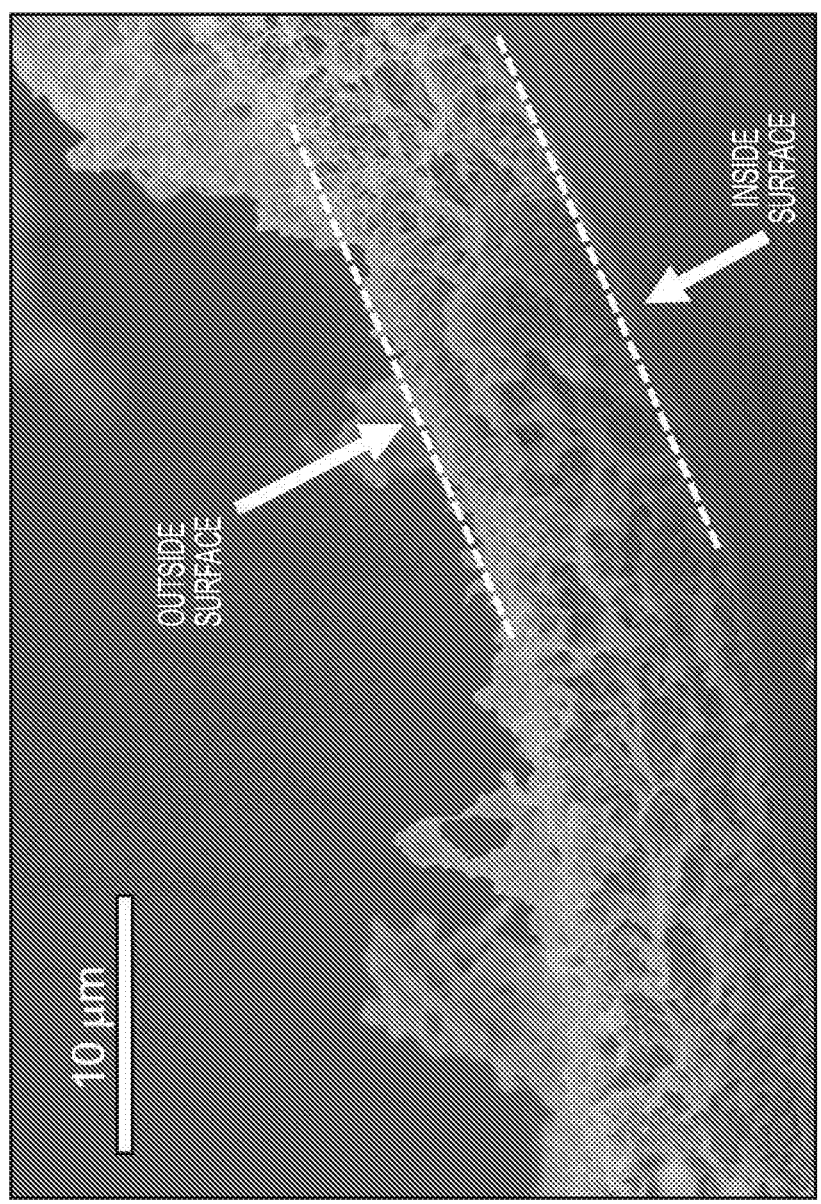
FIG. 5 shows an SEM photograph of the porous outer sheath of a modified suture. The interconnected pores go through the entire thickness of the sheath.
Figure 7A:
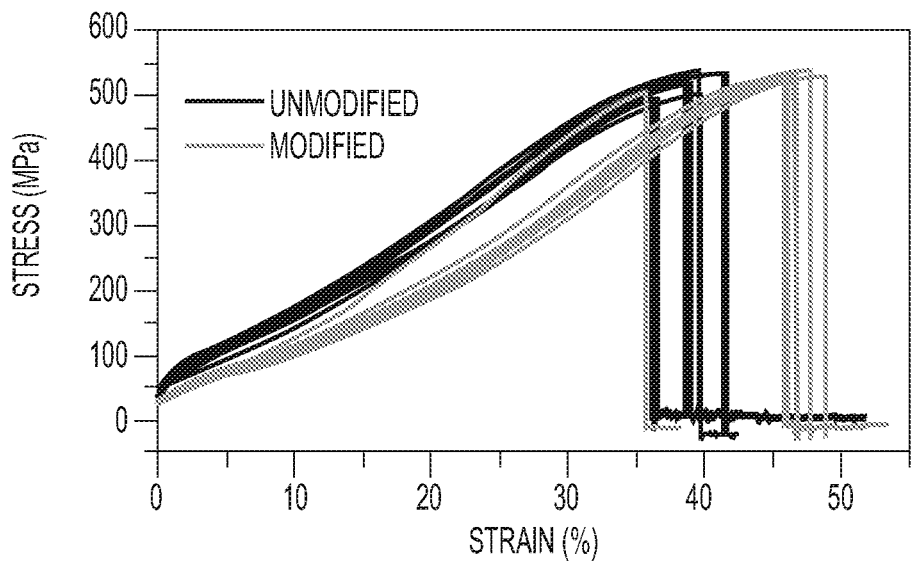
FIGS. 7A-7E show the results of tensile mechanical testing of the unmodified and modified sutures: stress-strain behavior (FIG. 7A), maximum stress (FIG. 7B), yield strain (FIG. 7C), strain at maximum stress (FIG. 7D), and modulus (FIG. 7E). N=7 for the unmodified samples and n=6 for the modified samples: *$p<0.05$ (by t-test) indicates significant difference between the two types of samples.
Figure 7B:
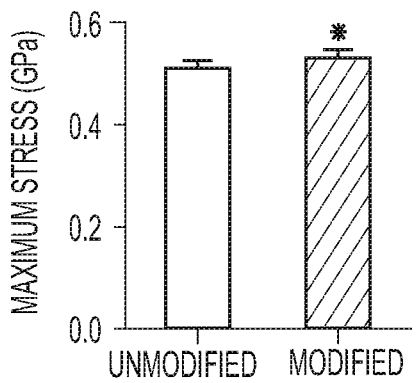
Figure 7C:
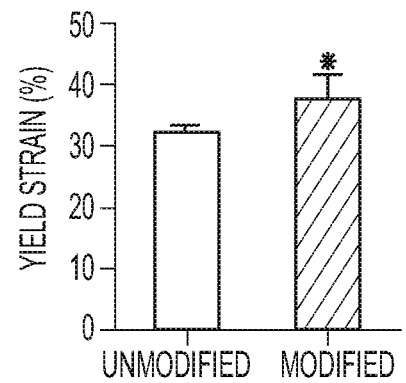
Figure 7D:
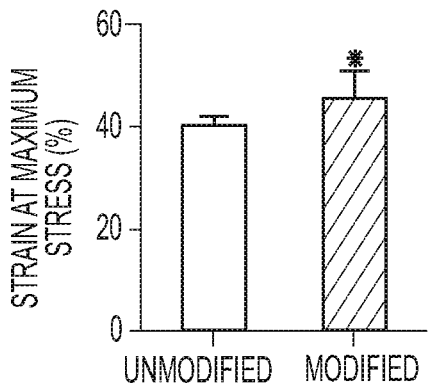
Figure 7E:
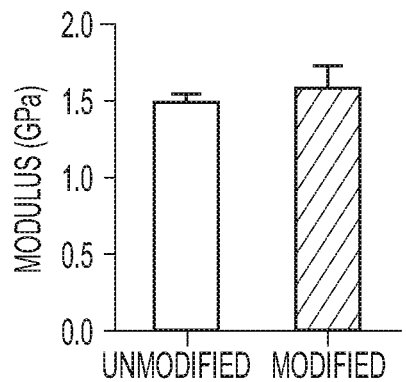

FIGS. 2A-D show typical scanning electron microscopy (SEM) images of the sutures before and after the modification. The original cable-type structure was retained during the modification, with packed filaments bundled by an outer sheath with a thickness of about 10 micrometers (FIG. 2A and FIG. 2B). The unmodified suture showed smooth surfaces. In contrast, the modified suture had a highly porous surface, with pore sizes in the range of 0.5 to 5 micrometers (FIG. 2C and FIG. 2D). The micrometer-sized pores were generated through the entire cross-section of the sheath (FIG. 5). By varying the calcium concentration, both the porosity and pore size were controlled (FIG. 6A-F). Since the inner filaments are the major contributors to the mechanical properties of a suture, the goal was to avoid modifying these inner filaments. Indeed, there were very few pores on the surfaces of the inner filaments.

The tensile mechanical properties of the sutures, with and without modification, were evaluated. Results are shown in FIGS. 7A-E. The two groups of stress-strain curves show similar patterns, indicating that the modification did not have a substantial impact on the mechanical properties of the sutures. There was no significant difference in modulus when comparing the unmodified to modified sutures. The moduli were 1.49±0.03 gigapascals and 1.59±0.13 gigapascals for the unmodified and modified sutures, respectively. The maximum stress increased, from 506.6±17.2 megapascals for the unmodified sutures to 530.4±14.5 megapascals for the modified sutures ($p<0.05$), at least in part due to the formation of calcium-nylon 6 complex. The strain at maximum stress and the yield strain of the modified sutures also increased by ~16% when compared with the unmodified sutures ($p<0.05$). Almost all of this increase occurred in the low stress, toe-portion of the stress-strain curve. As expected, the lack of modification to the inner filaments of the suture resulted in retention of mechanical properties, despite the creation of pores in the outer sheath. The sutures tested were 4-0 caliber sutures. The mechanical properties are partially representative of the suture diameter, and thus may vary according to the suture size. Nonetheless, for a given suture size, the mechanical properties of a modified and unmodified version will be substantially consistent.

Figure 9:
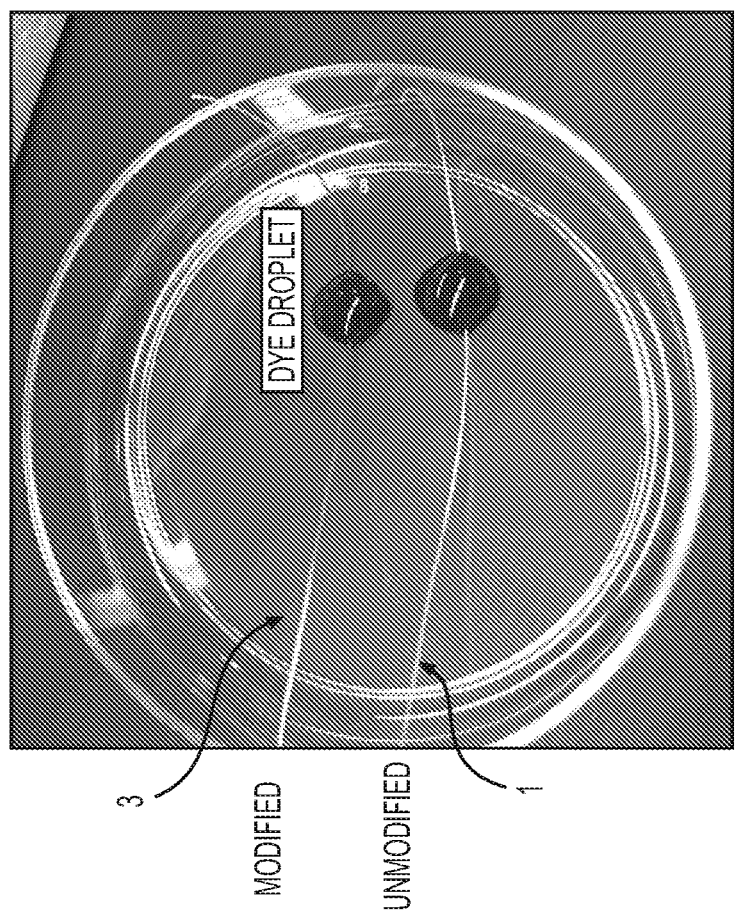
FIG. 9 shows a photograph demonstrating the capillary effect in the modified suture covered by a porous sheath. Unmodified and modified sutures were inserted through a droplet (supported on a 35 centimeter petri dish) of aqueous solution containing 1 milligram per milliliter Rhodamine B and 20 milligrams per milliliter fibrinogen. In less than 10 seconds, the red dye can be clearly seen along the modified suture on both sides of the droplet, while no dye was observed on the unmodified suture. The capillary action is of great benefit for the loading of releasable components dissolved in an aqueous solution.
Figure 10:
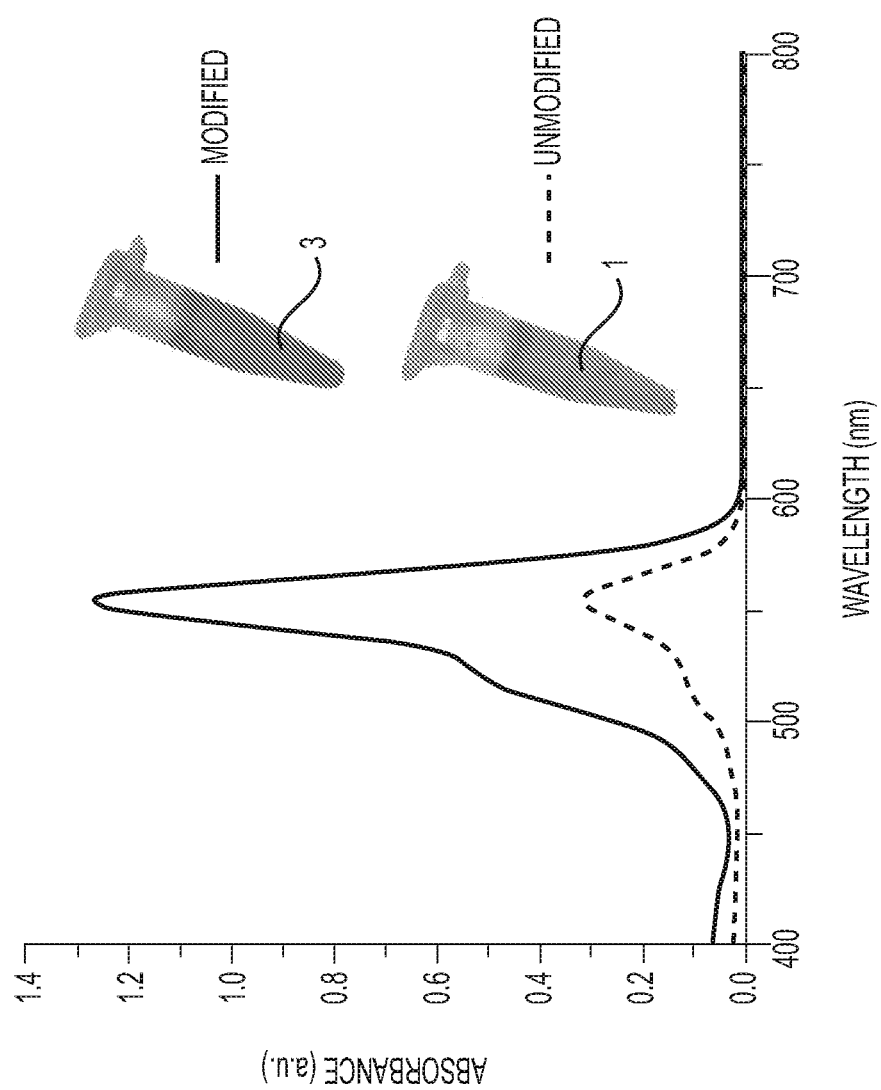
FIG. 10 shows the dye loading capacity for the modified and unmodified sutures. Both unmodified and modified sutures were soaked in Tris-buffered saline (TBS, pH=7.2) containing 20 milligrams per milliliter fibrinogen and 1 milligram per milliliter Rhodamine B for 2 hours at room temperature. The dye-loaded sutures were then placed in a tube containing 1 milliliter of DI water. The tubes were put on a shaker to accelerate the release. After 72 hours, the amount of dye released was quantified using a UV-vis spectrometer. By calibrating against a standard curve of Rhodamine B of known concentrations, the dye loaded into the unmodified and modified sutures were determined as ~208 nanograms per centimeter and ~847 nanograms per centimeter, respectively, demonstrating a nearly four-fold increase of loaded dye in the modified suture when compared with the unmodified suture.

A major objective was to increase the amount of a releasable component that can be loaded into a suture. Upon modification, infiltration of releasable component molecules into the voids among the inner filaments can be readily achieved via the interconnected pores created in the sheath. FIGS. 8A-D demonstrate the validation of the loading mechanism via fluorescence micrographs of the cross-sections of loaded sutures. A water-soluble dye (Rhodamine B, FIGS. 8A-8B) and a dye-labeled protein (FITC-BSA, FIGS. 8C-8D) were used as model systems of small and large molecules, respectively, to compare the unmodified suture 1 to the modified suture 3. Both the dye (FIG. 8B) and protein (FIG. 8D) can be clearly observed inside the modified suture 3, filling the void space among the filaments. For the unmodified suture 1, however, both the small dye molecules (FIG. 8A) and the protein (FIG. 8C) can only be observed on the outer surface. This result indicates that the sheath surrounding the filaments in the unmodified sutures cannot be easily penetrated by molecular species, whereas the porous sheath of the modified sutures can be used to access the voids among the inner filaments for the loading of small molecules and macromolecules. As further shown in the SEM photographs of FIGS. 4A and 4B, the capillary effect resulting from the interconnected pores and the concentration gradient of molecules in the solution effectively drove the fibrin carrier material through the pores and into the voids inside the sutures (FIG. 4B). The capillary action caused by the porous structure enhanced the loading of releasable components into the sutures. A simple demonstration of this capillary effect is shown in FIG. 9. Quantification of the released dye demonstrated a nearly four-fold increase of dye loading for the modified sutures compared to the unmodified sutures (FIG. 10). Furthermore, the integrity of the modified porous sheath 3 was demonstrated by the retention of loaded dye in modified sutures that were passed through a bovine tendon ten times (FIGS. 11A-E).

Figure 12:
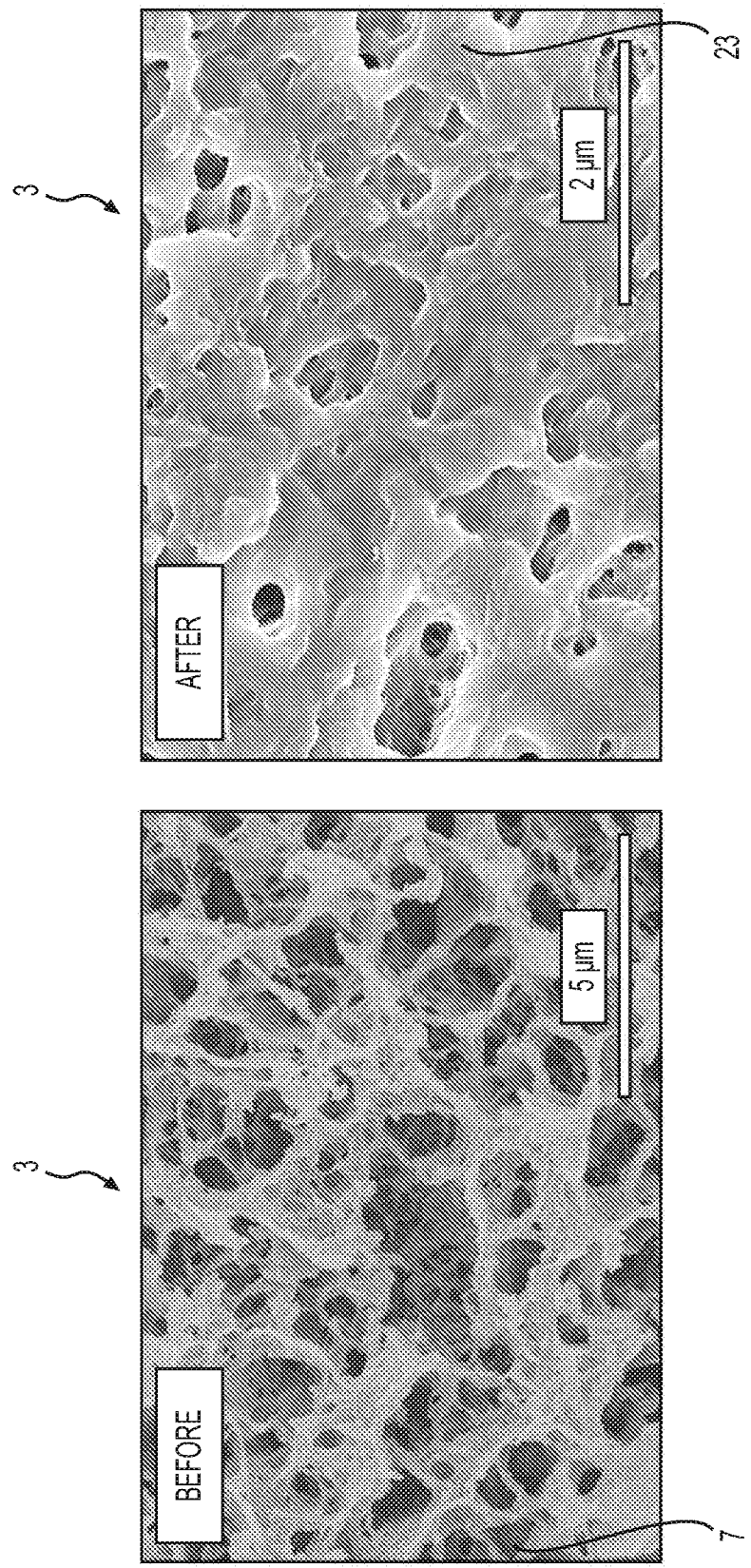
FIG. 12 shows an SEM image of the surface of a modified suture (left) before and (right) after loading with fibrin. The modified suture was immersed in TBS containing 20 milligrams per milliliter fibrinogen overnight at 4 degrees Celsius. Fibrin was formed by soaking the above suture in TBS containing 2 Units per milliliter thrombin and 40 milliMolar calcium chloride at room temperature for 2 hours. The fibrin-loaded suture was then dried for SEM characterization. The uneven holes were filled with fibrin, creating a smoother surface that may ease suture passage through tissues.
Figure 13A:
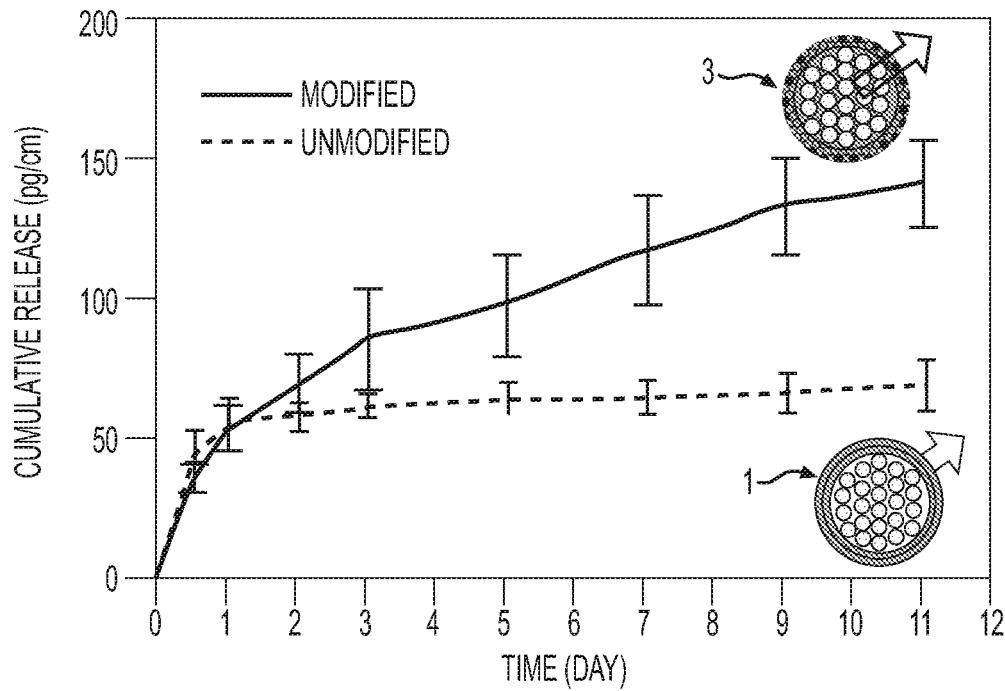
FIGS. 13A and 13B show results of a PDGF release study.
Figure 13B:
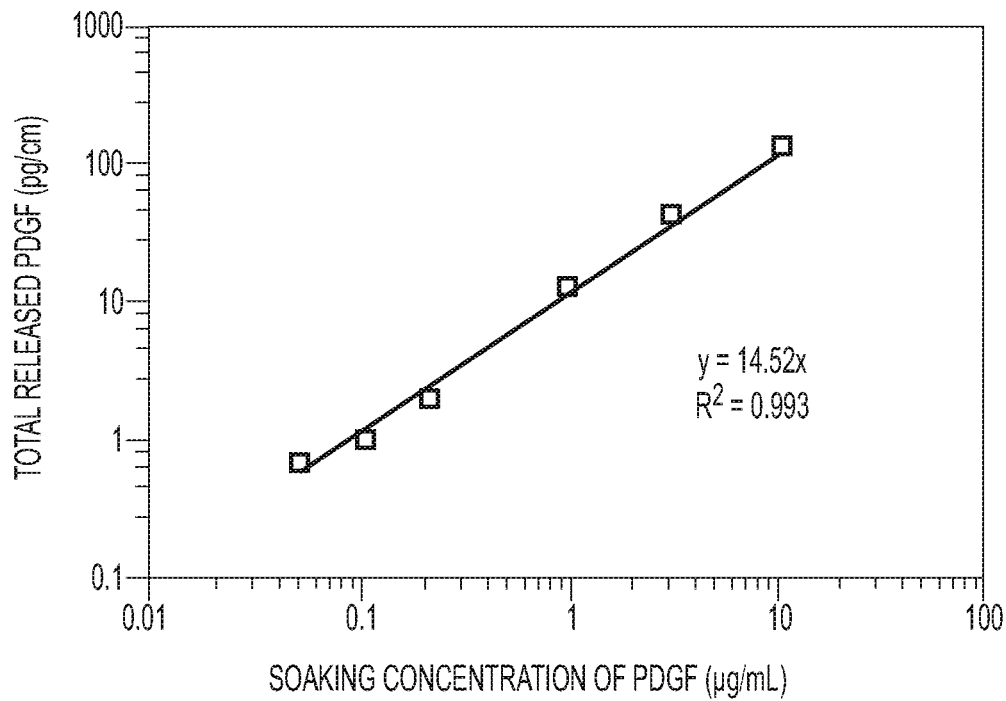

A second major objective was to release releasable components in a sustained manner from sutures. To demonstrate that the porous sheath on the modified suture (which allowed the releasable components to infiltrate into the suture through capillary action) can also serve as a physical barrier to slow the subsequent release process, recombinant human platelet-derived growth factor-BB (PDGF) was used as a model growth factor and fibrin as a carrier material. PDGF promotes chemotaxis and mitogenesis of mesenchymal cells, including tendon fibroblasts and mesenchymal stem cells. PDGF has been successfully used to promote tendon healing, including enhancing the collagen organization, mechanical function, and vascularity. Fibrin was used as a carrier material owing to its current clinical acceptance and the interactions it can have with endogenous factors, such as PDGF, TGF-β and VEGF, among others. To determine the release characteristics of the growth factor from the modified sutures 3, PDGF (10 micrograms per milliliter) was loaded into the sutures together with fibrin carrier material 23 (see FIG. 12, a typical SEM image of modified sutures after fibrin loading). FIG. 13A shows the cumulative release of PDGF from the modified sutures 3 as determined over a period up to 11 days. The release kinetics can be described using a two-stage model. The first stage shows a burst release and the second stage is characterized by a sustained release. For the first stage, approximately 38% of the loaded growth factor was released within the first 24 hours for modified sutures. In contrast, 81% of the growth factor was released from the unmodified sutures 1 within only 24 hours. In the second stage of release, for modified sutures 3, the growth factor (presumably trapped in the spaces among the inner filaments) was released through the fibrin network via the porous sheath in a sustained manner from day 2 to day 11. Furthermore, the total released growth factor from the modified sutures 3, that is, the dosage, was linearly dependent on the initial concentration of PDGF used for loading, in the range of 50 nanograms per milliliter to 10 micrograms per milliliter for this study ($R^2$=0.99; n=3 for each group), as shown in FIG. 13B. Delivery of growth factors at specific dosages within the first three weeks is critical for tendon healing. Therefore, the sustained and controlled release of releasable components from sutures presented here has a great potential for enhancing tendon repair.

Figure 15:
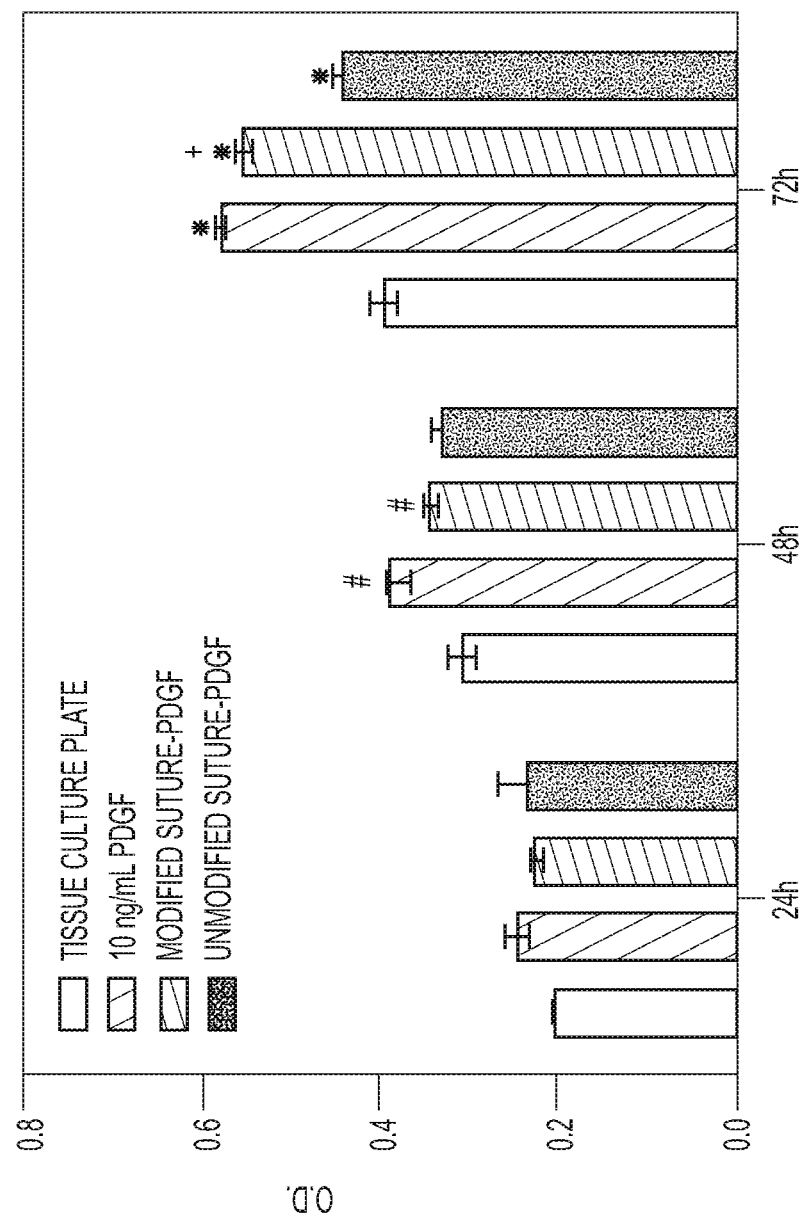
FIG. 15 shows PDGF released from the modified sutures enhancing the proliferation of hMSCs. To test the bioactivity of the PDGF released from the sutures, ~8,000 cells were seeded onto and around sutures in 24-well plates. Cells were cultured in the absence of PDGF (tissue culture plate group) as a negative control group and PDGF in the media at a concentration of 10 nanograms per milliliter as a positive control group. Cells were also cultured in the presence of unmodified and modified sutures loaded with 10 micrograms per milliliter PDGF. Cellular activity was quantified using the 3-(4,5-dimethylthiazol-2-yl)-2,5-diphenyltetrazolium bromide (MTT) assay (Invitrogen). For each time point (24, 48, and 72 hours), three samples were analyzed for each group. Assays were carried out in 24-well plates, and 500 microliters of MTT solution in PBS was added to each well and incubated at 37 degrees Celsius for 4 hours. Culture medium was then withdrawn, and 200 microliters of dimethyl sulfoxide was added to each well to dissolve the formazan crystals completely. Absorbance was measured at 560 nanometers using a microplate reader (Infinite F200 Pro, TECAN). All final data were normalized to the length of the sutures used. There was a significant difference between the unmodified and modified sutures at 72 hours. # Indicates $p<0.05$ for the O.D. values compared with the reference sample. * Indicates $p<0.05$ for the O.D. values compared with reference sample. + Indicates $p<0.05$ for the O.D. values compared with the unmodified suture sample. N=3 for each group, statistical comparisons were made via two-way ANOVA.
Figure 16A:
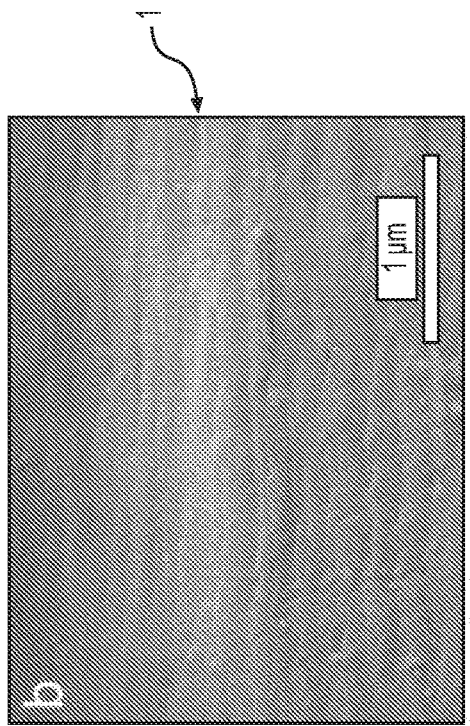
FIGS. 16A-16D show the results of the modification method to a monofilament suture (MONOMID 4-0, CP Medical, Inc.). The modification protocol was adjusted because most of the monofilament nylon suture is composed of nylon 66. Briefly, the sutures were soaked in a 1.6 Molar calcium chloride solution in methanol for 16 hours at room temperature. Afterwards, the swollen sutures were quickly frozen in liquid nitrogen and then freeze-dried in a vacuum overnight. The unmodified suture had a smooth surface (FIGS. 16A, 16B), while the modified sutures showed a highly porous surface (FIGS. 16C, 16D), with pore sizes in the range of 10-500 nanometers.
Figure 16B:
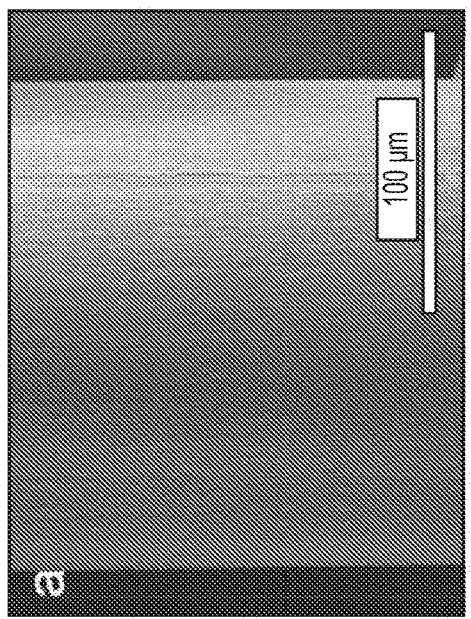
Figure 16C:
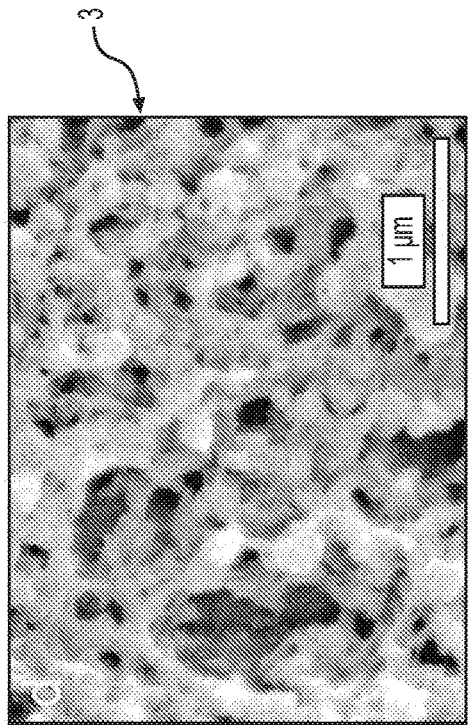
Figure 16D:
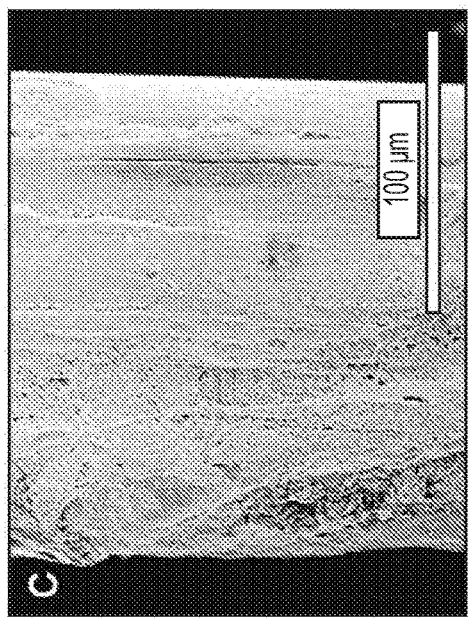

To evaluate potential cytotoxicity of the modified sutures and the PDGF-loaded modified sutures, human mesenchymal stem cells (hMSCs) were cultured on and around modified sutures 3 and unmodified sutures 1 and viability was assessed after 72 hours. As shown in FIGS. 14A-F, the hMSCs were viable after culture, indicating that the effects of any remaining chemicals from the preparation of porous sutures were negligible. To verify that the loading/release processes did not alter the bioactivity of the releasable component 11, hMSCs were cultured in the presence of 10 nanograms per milliliter PDGF and PDGF-loaded sutures (FIG. 15). The results indicate that the released PDGF retained its biologic activity and supported the proliferation of hMSCs. Recent reports have successfully demonstrated the potential for combinatory use of growth factors (e.g., bFGF and PDGF) and stem cells (e.g., adipose-derived mesenchymal stem cells and bone marrow stromal cells) for tendon repair in vivo. The suture-based release of these growth factors would simplify delivery of these factors alone or in combination with stem-cell therapies for more effective tendon repair. Furthermore, suture-based release would deliver these growth factors directly at the injury site and within the repaired tissue, where they can guide the healing response.

In summary, a simple and versatile method has been developed for generating surgical sutures with porous sheaths without compromising their mechanical properties. This method can also be used to generate pores on the surface of monofilament sutures (FIGS. 16A-D). The modified sutures showed an improvement in loading capacity and a sustained release of biologically active PDGF over a period of at least 11 days. This delivery system based on porous sutures can be used for the repair of load-bearing connective tissues such as tendons. Additionally, it can be used for the delivery of antimicrobials after wound closure and long-term pain-relief post-surgery. It can further provide a versatile platform for drug delivery in clinics. Finally, the pores can be loaded with a mixture of a drug and a phase-change material such as a fatty acid, for example to trigger drug release and control the release profile with a near-infrared laser.

Experimental Section

Preparation of Modified Sutures.

Unmodified sutures (Supramid® 4-0, cable-type, S. Jackson Inc., Alexandria, Va.) were purchased from S. Jackson Inc. The inner filaments were made of nylon 66 while the sheath was comprised of nylon 6. Sutures with porous sheaths were prepared using a swelling and freeze-drying procedure. Briefly, the unmodified sutures were cut into a certain length and soaked in a 500 milliMolar calcium chloride solution in methanol for 24 hours at room temperature. Afterward, the swollen sutures were quickly frozen in liquid nitrogen and then freeze-dried in a vacuum overnight. Since all the reagents used in this process were water-soluble, their residues can be readily removed by rinsing the samples with water.

Mechanical Testing.

The unmodified and modified sutures were pulled in uniaxial tension using a material testing machine (5866; Instron Corp., Norwood, Mass.), as described previously. A suture was carefully placed in a jig consisting of a low-friction spool and a clamp grip, which was pulled upward at 1.0 millimeters per second to apply tension to the suture. The gauge length between the suture grips was 110 millimeters for all the samples at the beginning of the test. Maximum stress, yield strain, strain at maximum stress, and modulus were determined from the stress—strain curves.

Preparation and Characterization of Releasable Component-Loaded Sutures.

The releasable component-loaded sutures were prepared in a biological safety cabinet and all the solutions were filtered through 0.22 micrometer filters to ensure sterility. The unmodified and modified sutures were sterilized with 75% ethanol and then immersed in Tris-buffered saline (TBS, pH=7.2) containing 20 milligrams per milliliter fibrinogen and recombinant human PDGF-BB at varying concentrations (0.05, 0.1, 0.2, 1, 3, and 10 micrograms per milliliter) overnight at 4 degrees Celsius. The sutures loaded with fibrinogen and PDGF were then soaked in TBS containing 2 Units per milliliter thrombin, $40 \times 10^{-3}$ Molar calcium chloride, and the same concentration of PDGF used in the previous step at room temperature for 2 hours. The samples were stored in a sterile tube at 4 degrees Celsius prior to further use. Both small dye molecules (Rhodamine B) and proteins (FITC-labeled bovine serum albumin, BSA) were used to evaluate the loading capacity of the sutures, the loading procedures of which were the same as PDGF. Laser confocal fluorescence microscopy (LSM 700, Zeiss, Oberkochen, Germany) was used to resolve the distribution of the dyes and dye-labeled proteins in each suture.

Quantification of PDGF Release.

Different groups of PDGF/fibrin/sutures (porous suture with 0.05, 0.1, 1, 3, and 10 micrograms per milliliter PDGF, n=3 and unmodified suture with 1.0 micrograms/milliliter PDGF, n=3 per group) with a length of 3 centimeters each were incubated in 0.2 milliliters of PBS at 37 degrees Celsius and an aliquot of the solution was collected at each time point. After each collection, 0.2 milliliters of fresh PBS was added to retain the solution at a fixed total volume. The collected aliquots were stored at −20 degrees Celsius before the amount of PDGF from each sample was quantified using an enzyme-linked immunosorbent assay (ELISA). The absorbance was read with a microplate reader (Synergy H4™ Multi-Mode Plate Reader, Biotek, Winooski, Vt., U.S.A.). The concentration of PDGF from each sample was determined from a calibration curve derived from PDGF solutions with known concentrations.

Cell Culture and Live/Dead Staining.

hMSCs were cultured in basal medium containing low-glucose Dulbecco's Modified Eagle Media, supplemented with 10% fetal bovine serum. Live/Dead staining of hMSCs on unmodified suture, modified suture, and 10 micrograms per milliliter PDGF-loaded porous suture using a Live/Dead staining kit (Invitrogen, Waltham, Mass.). After 72 hours, the culture medium was removed and the samples were washed gently with Dulbecco's phosphate-buffered saline. Then, 500 microliters of Live/Dead stain was added per well and incubated for 30 minutes at 25 degrees Celsius. Finally, the samples were washed with PBS and observed using a fluorescence microscope (DMI 6000B, Leica, Wetzlar, Germany) at excitation wavelengths of 488 nanometers (green) and 533 nanometers (red).

Statistics.

The data from mechanical testing were analyzed using Student's t-test in Microsoft Excel. Cell proliferation results were compared using two-way analysis of variance test (ANOVA) in GraphPad Instat software (GraphPad Software Inc., La Jolla, Calif., U.S.A.). Statistical significance was set at $p<0.05$.

Example 2

Figure 19:
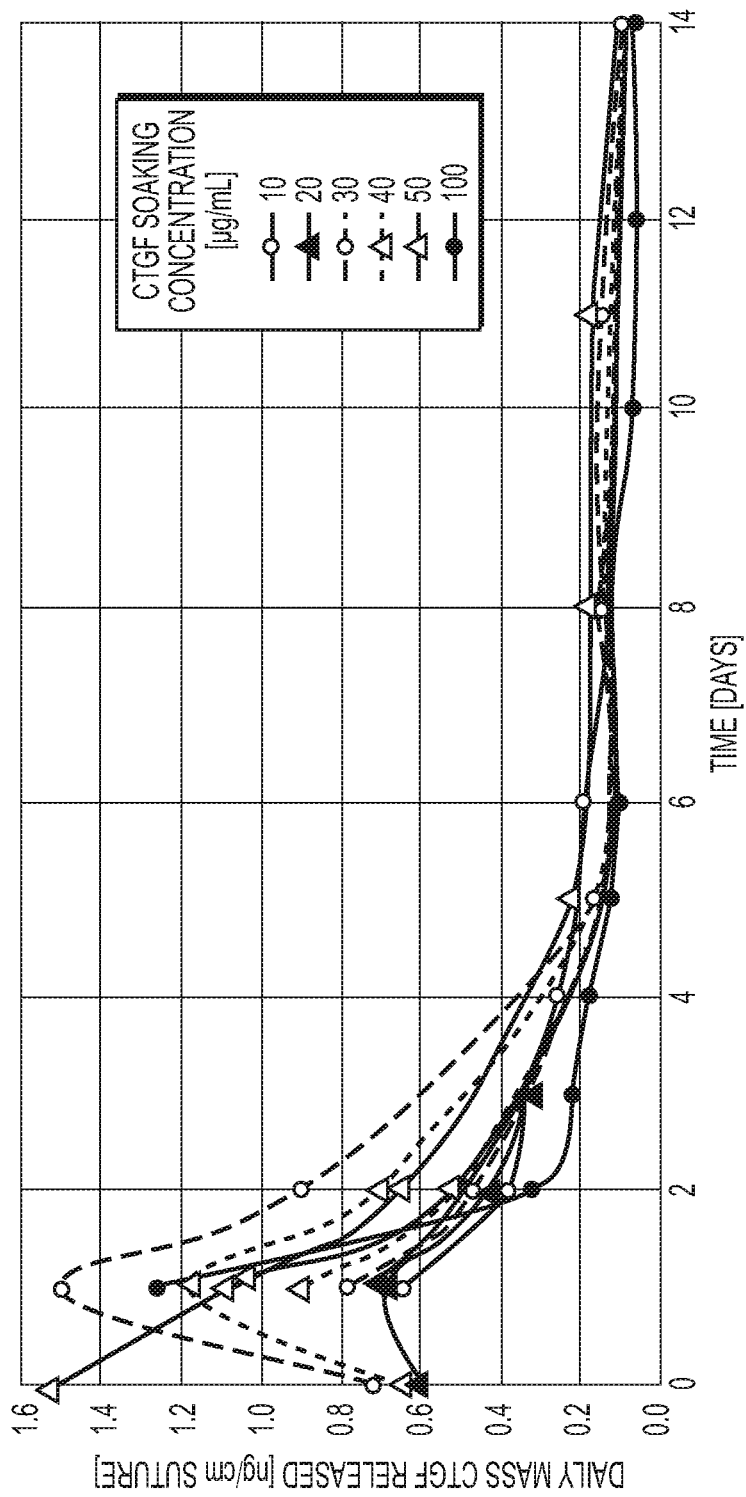
FIG. 19 shows cumulative connective tissue growth factor (CTGF) release profiles for porous sutures loaded with a range of CTGF soaking concentrations (10-100 micrograms per milliliter) within a heparin/fibrin-based delivery system (HBDS), in vitro. Porous sutures loaded with HBDS+CTGF showed an initial burst followed by sustained release over the first 14 days. The 30 micrograms per milliliter CTGF group was the highest loading concentration that did not form precipitate in solution. Within the narrow concentration range depicted here, all soaking concentrations yielded similar sustained release profiles.

This example demonstrates sustained in vitro release of connective tissue growth factor (CTGF) from modified sutures over 14 days. Sutures demonstrated sustained release of CTGF over at least 14 days in vitro (FIG. 19). Loading capacity was partially limited by CTGF and heparin binding delivery system (HBDS) component solubility in the fibrinogen and thrombin solutions used during loading (Table 1). Therefore, while the CTGF loaded into the soaking buffer progressively increased with each subsequent concentration, the effective concentration decreased when precipitate formed above 30 micrograms per milliliter CTGF. The maximum CTGF release was observed from porous suture segments loaded with 30-50 micrograms per milliliter CTGF/HBDS solution, corresponding with the maximum soluble CTGF/HBDS concentration in the fibrinogen loading solution. Porous modified sutures loaded in 30 micrograms per milliliter CTGF/HBDS demonstrated burst release of 0.50-1.50 nanograms CTGF per centimeter suture per day for the first few days, followed by sustained release of approximately 0.15 nanograms CTGF per centimeter suture per day through day 14. Since approximately 70 millimeters of suture is delivered within 3 millimeters of the repair site in the traversing strands and the terminal knot of a Winters-Gelberman style flexor tendon repair, this release level corresponded to concentrations of 60-150 nanograms per milliliter daily burst delivery and 10-20 nanograms per milliliter daily sustained release from suture within 3 millimeters of the tendon laceration site.

TABLE 1 precipitate formation in loading buffer containing fibrinogen + CTGF/HDBS components

| CTGF soaking concentration (micrograms per milliliter) | Precipitate formation |
|---|---|
| 10 | no visible precipitate |
| 20 | no visible precipitate |
| 30 | very slight precipitate, disappeared within 1-2 seconds |
| 40 | definite precipitate, disappeared after 5-10 seconds |
| 50 | most, but not all, precipitate re-dissolved over time |
| 100 | substantial precipitate, did no re-dissolve |

Experimental Section

Sustained Growth Factor Release Methods.

Porous sutures, lyophilized after being washed with distilled water several times, were loaded with the recombinant human growth factor CTGF (BioVendor, Asheville, N.C., U.S.A.). CTGF was loaded in a fibrin/heparin binding delivery system (HBDS) for sustained release, as described previously. The lyophilized sutures were first sterilized with ethylene oxide gas, then care was taken to maintain sterility before use. Sutures only came into contact with sterile solutions (0.2 micrometer-filtered) in a sterile biosafety cabinet, using autoclaved surgical instruments and sterile surgical gloves. All pipette tips, tubes, and tools were either silanized or rinsed with TBS containing 0.1% bovine serum albumin (BSA) prior to use to block inadvertent protein binding. To coat with CTGF/HBDS, sterile sutures were first either cut into 15 millimeter pieces for in vitro release profile evaluation or left as 30 centimeter looped suture with a needle for in vivo surgical implantation. Sutures or suture segments were then submerged in TBS (pH 7.4) containing 0.1% weight by volume BSA (Sigma Aldrich, Saint Louis, Mo., U.S.A.), 20 milligrams per milliliter human fibrinogen (plasminogen depleted, 95% clottable proteins; EMD Millipore, Billerica, Mass.), and CTGF/HBDS components at 4 degrees Celsius overnight. The fibrinogen- and CTGF/HBDS-loaded sutures were then immersed in TBS containing 0.1% weight by volume BSA, 20 Units per milliliter thrombin (Sigma Aldrich, Saint Louis, Mo., U.S.A.), and 13.7 milliMolar calcium chloride for 2 hours at 37 degrees Celsius to polymerize the fibrinogen-based carrier material precursor solution to a fibrin carrier material. Suture samples were washed by rinsing in TBS with 0.1% weight by volume BSA to remove unbound CTGF before collecting release profiles in vitro or implanting suture in vivo.

The CTGF/HBDS components used for the two loading steps included: (i) a bi-domain HBDS peptide, (ii) heparin (H3393, Sigma Aldrich, Saint Louis, Mo., U.S.A.), and (iii) CTGF at a 4:1:(1/135) stoichiometric molar ratio, calculated based on final CTGF concentrations (10, 20, 30, 40, 50, or 100 micrograms per milliliter for in vitro release studies; 0 or 30 microgram per milliliter for in vivo surgical studies). HBDS peptide consisted of a factor XIIIa substrate derived from alpha2-plasmin inhibitor at the N-terminus and a C-terminal heparin-binding domain from anti-thrombin II (sequence dLNQEQVSPK(betaA)FAKLAARLYRKA-NH2, where dL denotes dansyl leucine, purity>95%; GenScript, Piscataway, N.J., U.S.A.). The bi-domain peptide was covalently cross-linked to fibrin during polymerization by the transglutaminase activity of factor XIIIa. The peptide electrostatically immobilized heparin to the matrix, which in turn immobilized the heparin-binding growth factor, CTGF, preventing diffusion away from the matrix.

After loading porous modified suture with varying concentrations of CTGF/HBDS (0, 10, 20, 30, 40, 50, 100 micrograms per milliliter, n=2 per group), 15 millimeter suture segments were incubated in 70 microliters of TBS containing 0.1% weight by volume BSA in a 0.6 milliliter tube at 37 degrees Celsius. Aliquots of all 70 microliters of solution were collected at each time point and replaced with fresh TBS with 0.1% weight by volume BSA. The collected aliquots were placed in a silanized tube, centrifuged for 3 minutes at 16,100 g, and stored at −80 degrees Celsius before the amount of CTGF was quantified using an enzyme-linked immunosorbent assay (BioOcean®, Shoreview, Minn., U.S.A.). The absorbance was read with a microplate reader (Cytation™ 5 Plate Reader, BioTek, Winooski, Vt., U.S.A.) and the concentration of CTGF from each sample was determined from a calibration curve derived from CTGF solutions with known concentrations.

Example 3

Figure 17:
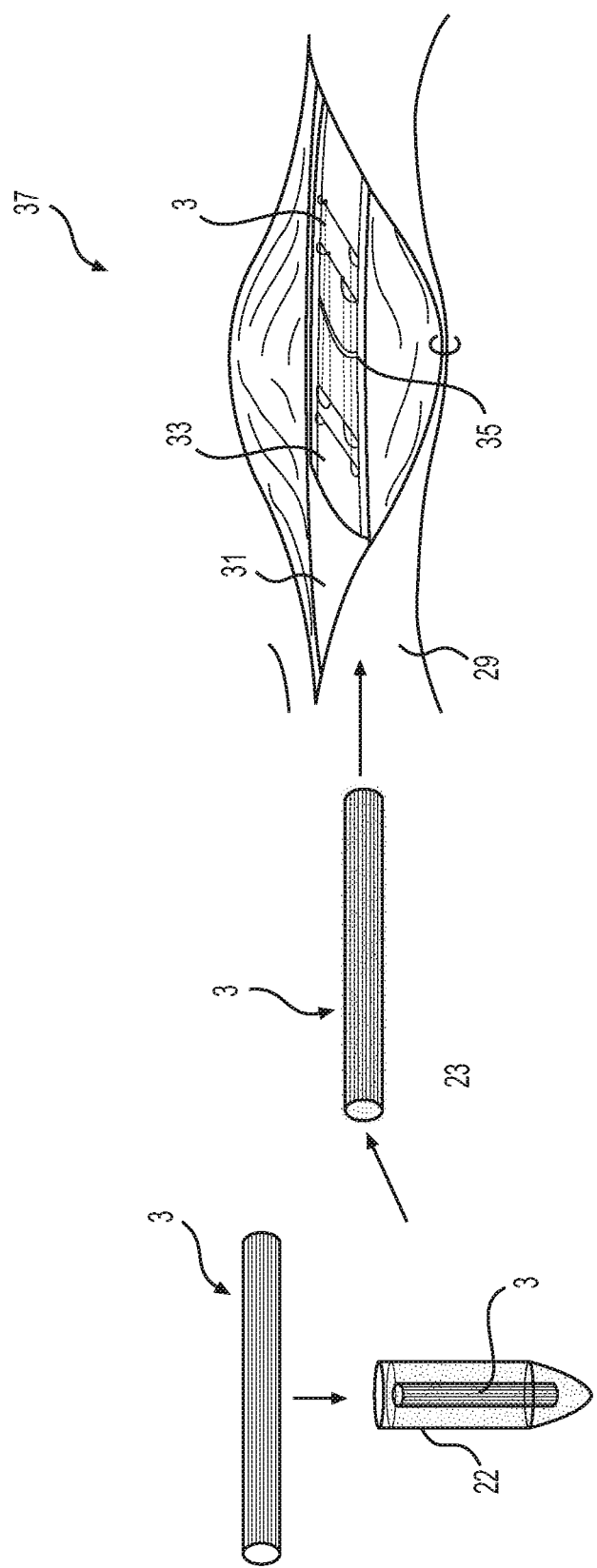
FIG. 17 shows a schematic for loading a modified suture with carrier material/releasable component and using the modified suture for tendon repair.
Figure 18A:
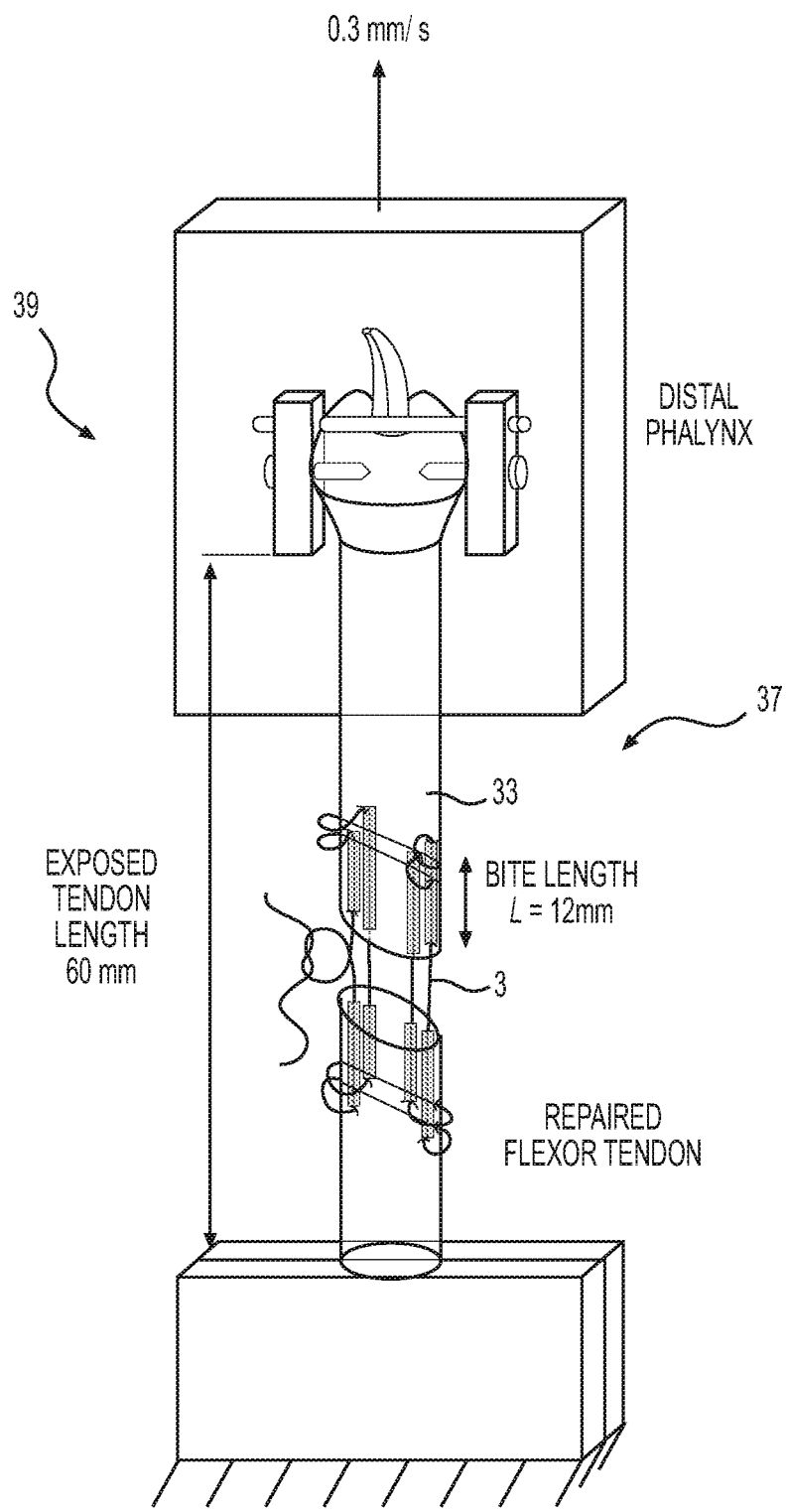
FIGS. 18A-18C show setup and results for tensile mechanical testing of the unmodified and modified sutures in an 8-stranded Winters-Gelberman flexor digitorum profundus tendon repair model.
Figure 18B:
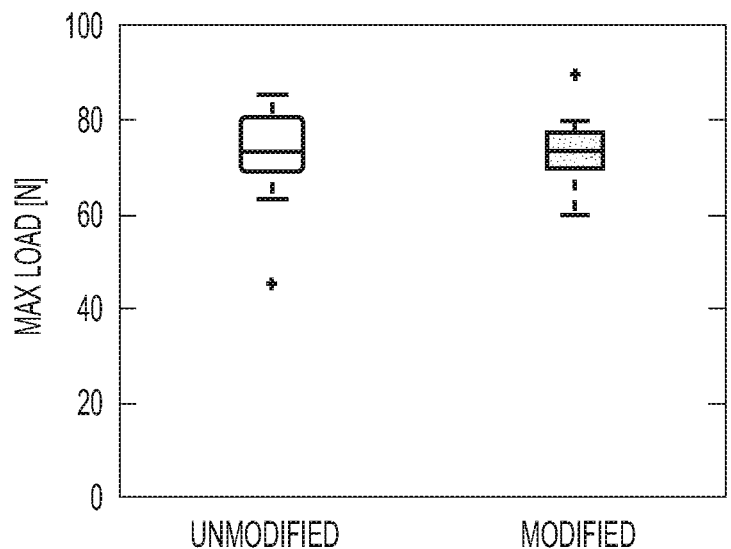
Figure 18C:
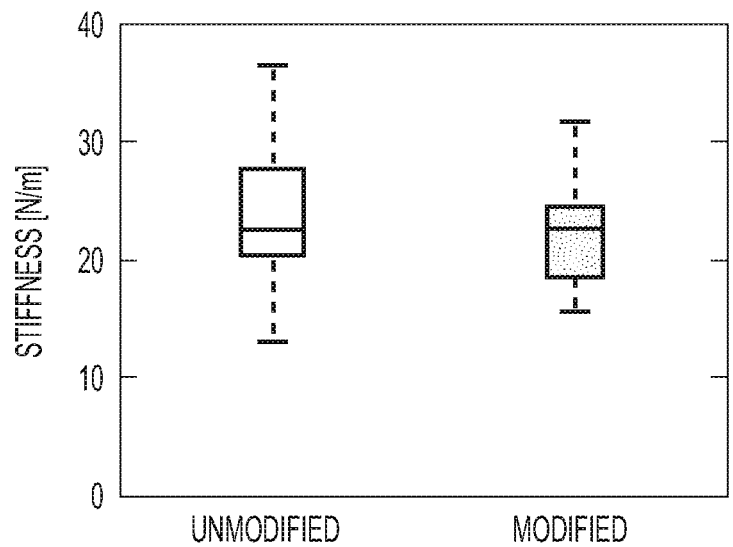

In this example, the biomechanics of modified sutures were tested using a clinical-style repair model. The schematic shown in FIG. 17 demonstrates the loading of a modified suture 3 with carrier material precursor solution 22. The modified suture 3, loaded with the polymerized carrier material 23, is sutured into the flexor digitorum profudus of cadaver canine forepaw samples. FIG. 17 shows this clinical-style model 37 (skin 29, tendon sheath 31, tendon 33, and suture 3 bridging the transection 35). FIG. 18A shows the clinical-style model 37 loaded on the testing apparatus 39. As shown in FIG. 18B, the repairs with unmodified and modified sutures had failure forces of 72.7±11.3 Newtons and 74.1±8.0 Newtons, respectively. The repairs with porous sutures had non-inferior failure force ($p<0.05$). The repair stiffnesses with unmodified and modified sutures were 24.0±7.0 Newtons per meter and 22.6±4.6 Newtons per meter, respectively, as shown in FIG. 18C. The repairs with modified sutures also had non-inferior stiffness ($p<0.05$).

Experimental Section

Clinical-Style Repair Biomechanics Methods.

Cadaver canine forepaw samples were obtained postmortem from an unrelated study and frozen at −20 degrees Celsius before use. Unmodified and porous sutures were used to perform 8-stranded 4-0 caliber Winters-Gelberman flexor digitorum profundus (FDP) tendon repairs by a highly experienced orthopedic hand surgeon (n=10 for modified, porous sutures and n=11 for unmodified sutures). Cadaver tendons were first surgically exposed and sharply transected in the anatomical Zone 2 (i.e., between the flexor digitorum superficialis insertion distally and the origin of the fibro-osseous flexor sheath proximally, commonly known as the zone from the distal palm to the proximal interphalangeal joint). Eight suture strands were passed through the tendon tissue in 4 bundles of 2 strands each. These strands passed about 12 millimeters into the tendon tissue proximal and distal to the transected surface of the tendon. Following this core suture placement, the epitenon was repaired using a 5-0 nylon epitenon suture. Following clinical-style repair, cadaver FDP tendons were carefully dissected out of the forepaw, disarticulating at the interphalangeal joint and leaving the distal phalynx (bone) attached to the FDP tendon. These dissected tendons were biomechanically evaluated as shown in FIG. 18A. Tendons were gripped by the distal phalynx and the proximal tendon to leave an exposed tendon gauge length of 60 millimeters between the grips. After 5 cycles of triangular waveform preconditioning up to 1 millimeter displacement, at a rate of 0.3 millimeter per second, samples were pulled in uniaxial tension using a material testing machine (5866; Instron Corp., Norwood, Mass., U.S.A., chosen because of a high capacity load cell) at 0.3 millimeter per second until failure. From the force-elongation curves, maximum force and stiffness (slope of the linear region) were determined.

Example 4

In this example, the biocompatibility of the porous sutures and the effects of CTGF delivery were evaluated in an in vivo canine intrasynovial flexor tendon repair model shown in FIG. 17. Flexor digitorum profundus tendon transections and repairs were performed with porous modified sutures loaded with 0 or 30 micrograms per milliliter CTGF in HBDS. There was only one tendon with a major gap (i.e., greater than 3 millimeters) among the 10 animals (20 tendons) examined post mortem. This tendon was repaired with control suture containing 0 microgram per milliliter CTGF. One animal pulled its paw partially up into the cast and had a minor 1.5 millimeter gap on the 0 microgram per milliliter control digit, and no gap on the 30 microgram per milliliter CTGF digit. There were no apparent indicators of inflammation or other negative effects at 14 days, with no or only very mild adhesions. This result positively contrasts with historical experience, where canine flexor tendon repairs are highly sensitive to inflammatory stimuli.

Experimental Section

Sterile Preparation Methods.

Sutures were sterilized using ethylene oxide gas. Using sterile-filtered solutions in a tissue culture hood/biosafety cabinet, the growth factor solutions were mixed with the heparin-binding delivery system (HBDS) components, adding all components except for fibrinogen. Protein blocking was performed in a silanized tube. All pipette tips were rinsed with a TBS+0.1% BSA solution (or an acetate buffer+ 0.1% BSA solution before drawing up the CTGF, to match the buffer). Using sterile surgical instruments and sterile surgical gloves, on a sterile drape within the tissue culture hood, ethylene oxide-treated porous sutures were removed and carefully untangled. Sutures with visible mechanical defects (burrs, fraying) were discarded. After fully untangling, sutures were folded it over ~5 times and placed into a sterile, empty 300 microliter PCR tubes or 600 microliter Eppendorf Tubes® (Eppendorf, Hamburg, Germany) that had been rinsed with TBS+0.1% BSA to block protein binding. Once the sutures were placed in these tubes, fibrinogen was added to the growth factor solution. The fibrinogen/growth factor solution with HBDS components was quickly transferred to the tubes with sutures for incubation. These tubes were capped with the needle sticking out, and then placed into a 50 milliliter sterile conical tube to retain sterility. The sutures were incubated at 4 degrees Celsius overnight. Similar protocols were used to mix and move suture into a thrombin/growth factor solution with HBDS components. This was incubated at 37 degrees Celsius for 2 hours to allow thrombin to cleave fibrinogen into fibrin for polymerization, thereby encapsulating the CTGF for sustained delivery, prior to moving to the operating room for surgical implantation. Again using sterile gloves and a sterile field, sutures were carefully detangled, rinsed in sterile TBS, and implanted.

Biocompatibility Testing.

To determine the biocompatibility of porous sutures and the effects of CTGF delivered in a sustained fashion via porous sutures, intrasynovial flexor tendon repairs were performed in canines (two repairs per animal, paired design comparing porous sutures to porous sutures loaded with CTGF; n=10 tendons per group). In the first group, the flexor digitorum profundus tendon of either the medial or lateral right forepaw digit was sharply transected at the level of the proximal interphalangeal joint (i.e. within the Zone 2, as described above) and repaired using a porous modified core suture, coated as described above with all HBDS components except for CTGF (Porous-control group). In the other group, the opposite flexor tendon in the same operated paw (2nd or 5th digit) was transected and repaired using a porous modified core suture coated with all HBDS components, including CTGF at a 30 micrograms per milliliter soaking concentration (CTGF+group). All repairs were performed using an 8-stranded Winters-Gelberman 4-0 core suture technique followed by a 5-0 nylon epitenon suture. Controlled passive motion exercise was applied to the digits postoperatively. The corresponding left digital flexor tendons served as normal controls (Normal group). All animals were euthanized 14 days after repair and evaluated at dissection for signs of repair site adhesions, gapping, rupture, and/or inflammation. All procedures were approved by Washington University's Animal Studies Committee.

While the invention has been described with reference to particular embodiments and implementations, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention will not be limited to the particular implementations disclosed herein, but that the invention will include all implementations falling within the scope of the appended claims.

REFERENCES

[1] M. Hattori, M. Saito, K. Okajima, K Kamide, Polym. J. 1995, 27, 631.

[2] B. Sun, Chin. J Poly. Sci. 1994, 12, 57.

What is claimed is:

1. A surgical suture material comprising;
an elongated outer sheath having an outer surface, an inner surface that defines a lumen, a plurality of pores extending between the lumen and the outer surface, and an amide-containing polymer material, the amide-containing polymer material comprising carbonyl oxygen atoms bonded to calcium ions throughout the cross-section of the outer sheath, and wherein the plurality of pores are generated from swelling the amide-containing polymer material in a swelling solution comprising calcium ions followed by freeze-drying,
a plurality of elongated filaments located within the lumen of the elongated outer sheath, and
a releasable component located in the lumen and able to move from the lumen through one or more pores of the plurality of pores for release from the suture material,
wherein the elongated outer sheath has a thickness of from about 6 to about 12 micrometers and the lumen has a diameter of greater than 100 micrometers, and
wherein the plurality of pores exhibit pore sizes in the range of 0.5 to 5 micrometers.

2. The surgical suture material of claim 1, wherein the polymer material is nylon, and carbonyl oxygen atoms of the nylon polymer chains form coordination bonds with the calcium ions.

3. The surgical suture material of claim 1, wherein the surgical suture material has a modulus of greater than or equal to 1.4 GPa.

4. The surgical suture material of claim 1, wherein the surgical suture material has an ultimate stress of greater than or equal to 0.5 GPa.

5. The surgical suture material of claim 1, wherein the surgical suture material has a strain at maximum stress of less than or equal to 38%.

6. The surgical suture material of claim 1, further comprising a fibrin carrier material located in the lumen and the pores of the elongated outer sheath, wherein the fibrin carrier material houses the releasable component.

7. The surgical suture material of claim 6, wherein the fibrin carrier material is configured to provide sustained release of a heparin binding growth factor from the elongated outer sheath.

8. The surgical suture material of claim 1, wherein the releasable component is a protein, a small molecule, or an ion.

9. The surgical suture material of claim 1, wherein the releasable component is an adhesive.

10. The surgical suture material of claim 1, wherein the filaments of the plurality of elongated filaments are axially aligned within the lumen, thereby defining axially aligned elongated spaces between the filaments, and the releasable component is housed in the elongated spaces between the elongated filaments in the lumen.

11. A method of loading the surgical suture material with the releasable component, according to claim 1, the method comprising;
swelling the surgical suture material in the swelling solution comprising calcium ions,
freeze-drying the surgical suture material, thereby introducing the plurality of pores that extend inward from the outer surface of the surgical suture material, and
filling at least some of the plurality of pores with the releasable component.

12. The method of claim 11, further comprising exposing the surgical suture material to a carrier material precursor solution comprising the releasable component, filling at least some of the plurality of pores with the carrier material precursor solution, and polymerizing the carrier material precursor solution to form a carrier material.

13. The method of claim 12, wherein the carrier material precursor solution comprises fibrinogen, and polymerizing further comprises exposing the carrier material precursor solution to thrombin and calcium chloride.

14. The method claim 11, wherein the releasable component is connective tissue growth factor (CTGF), and the CTGF concentration in the carrier material precursor solution is less than or equal to 50 micrograms per milliliter.

15. The method of claim 11, wherein the surgical suture material comprises the lumen, and the method further comprises filling at least part of the lumen with the releasable component.

16. The method of claim 11, wherein the swelling solution comprises calcium chloride in methanol, and the concentration of calcium chloride in methanol is 1.6 M or less.

17. The method of claim 11, wherein swelling the surgical suture material comprises incubating the suture in the swelling solution for from 16 to 28 hours.

18. The method of claim 11, wherein freeze-drying the surgical suture material comprises freezing the surgical suture material at −97 degrees Celsius or less and drying the surgical suture material under a vacuum.

* * * * *